US012583940B2

(12) United States Patent
Xu et al.

(10) Patent No.: US 12,583,940 B2
(45) Date of Patent: Mar. 24, 2026

(54) MONOCLONAL ANTIBODY WHICH TARGETS TFPI

(71) Applicant: SUZHOU ALPHAMAB CO., LTD., Jiangsu (CN)

(72) Inventors: Ting Xu, Jiangsu (CN); Xiaoxiao Wang, Jiangsu (CN); Ying Fan, jiangsu (CN); Yanrong Dong, Jiangsu (CN); Liping Chen, Jiangsu (CN); Jianyun Ji, Jiangsu (CN)

(73) Assignee: Suzhou Alphamab Co., Ltd., Jiangsu (CN)

( * ) Notice: Subject to any disclaimer, the term of this patent is extended or adjusted under 35 U.S.C. 154(b) by 869 days.

(21) Appl. No.: 17/639,139

(22) PCT Filed: Aug. 28, 2020

(86) PCT No.: PCT/CN2020/112057
§ 371 (c)(1),
(2) Date: Feb. 28, 2022

(87) PCT Pub. No.: WO2021/037197
PCT Pub. Date: Mar. 4, 2021

(65) Prior Publication Data
US 2022/0325000 A1      Oct. 13, 2022

(30) Foreign Application Priority Data
Aug. 29, 2019    (CN) .......................... 201910805428.6

(51) Int. Cl.
*C07K 16/38* (2006.01)
*A61P 7/04* (2006.01)
*A61K 39/00* (2006.01)

(52) U.S. Cl.
CPC ................ *C07K 16/38* (2013.01); *A61P 7/04* (2018.01); *A61K 2039/505* (2013.01); *C07K 2317/24* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,180,370 B1 * | 1/2001 | Queen .................... | A61P 19/02 |
| | | | 435/69.6 |
| 10,550,200 B2 * | 2/2020 | Pittman .............. | A61K 39/3955 |
| 2011/0098345 A1 | 4/2011 | Schaub et al. | |

FOREIGN PATENT DOCUMENTS

| | | |
|---|---|---|
| WO | WO 2010/017196 A2 | 2/2010 |
| WO | WO 2010/072687 A1 | 7/2010 |
| WO | WO 2010/072691 A1 | 7/2010 |
| WO | WO 2011/109452 A1 | 9/2011 |
| WO | WO 2012/001087 A1 | 1/2012 |

OTHER PUBLICATIONS

Wood, Jeremy P., et al. "Biology of tissue factor pathway inhibitor." Blood, The Journal of the American Society of Hematology 123.19 (2014): 2934-2943. (Year: 2014).*
Piche-Nicholas, Nicole M., et al. "Changes in complementarity-determining regions significantly alter IgG binding to the neonatal Fc receptor (FcRn) and pharmacokinetics." MAbs. vol. 10. No. 1. Taylor & Francis, 2018 (Year: 2018).*
Kipriyanov, Sergey M., and Fabrice Le Gall. "Generation and production of engineered antibodies." Molecular biotechnology 26.1 (2004): 39-60. (Year: 2004).*
Janeway, Charles A. "Immunobiology: The Immune System in Health and Disease." 2001 (Year: 2001).*
International Search Report corresponding to International Patent Application No. PCT/CN2020/112057 dated Dec. 23, 2020.
Efthymiou et al. (2018) "Antibodies Against TFPI and Protein C Are Associated With a Severe Thrombotic Phenotype In Patients With and Without Antiphospholipid Syndrome," Thrombosis Research, vol. 170, No. 07, pp. 60-68.

* cited by examiner

*Primary Examiner* — Michael Szperka
*Assistant Examiner* — Lia E Taylor
(74) *Attorney, Agent, or Firm* — JENKINS, TAYLOR & HUNT, P.A.

(57) ABSTRACT

Disclosed is a monoclonal antibody or an antigen binding fragment thereof which targets tissue factor pathway inhibitor (TFPI), and a medical use thereof.

19 Claims, 3 Drawing Sheets

Specification includes a Sequence Listing.

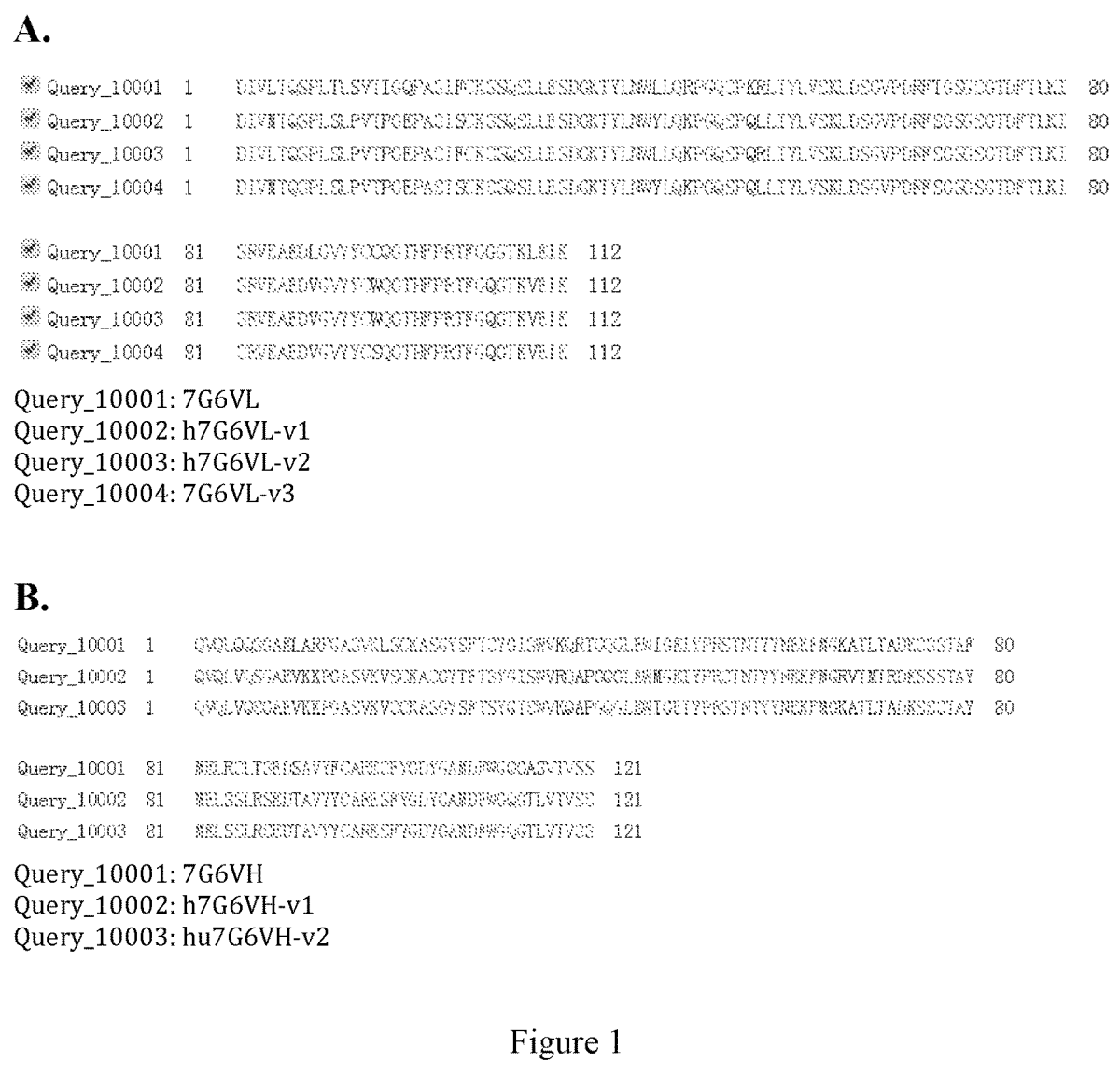

A.

| | | | |
|---|---|---|---|
| Query_10001 | 1 | DIVLTQSPLTLSVTIGQPACIFCKSSQSLLSSDGKTYLNWLIQRPGQSPKRLIYLVSKLDSGVPDRFTGSGSGTDFTLKI | 80 |
| Query_10002 | 1 | DIVMTQSPLSLPVTPGEPACISCKSSQSLLSSDGKTYLNWYLQKPGQSPQLLIYLVSKLDSGVPDRFSGSGSGTDFTLKI | 80 |
| Query_10003 | 1 | DIVLTQSPLSLPVTPGEPACIFCKSSQSLLSSDGKTYLDWLIQKPGQSPQRLIYLVSKLDSGVPDRFSGSGSGTDFTLKI | 80 |
| Query_10004 | 1 | DIVMTQSPLSLPVTPGEPACISCKSSQSLLESLGKTYLNWYLQKPGQSPQLLIYLVSKLDSGVPDRFSGSGSGTDFTLKI | 80 |

| | | | |
|---|---|---|---|
| Query_10001 | 81 | SRVEASLGVYYCQQGIHFPRIFGGGTKLEIK | 112 |
| Query_10002 | 81 | SRVEASDVGVYYCWQGIHFPRIFGQGTKVEIK | 112 |
| Query_10003 | 81 | SRVEAEDVGVYYCWQGIHFPRIFGQGTKVEIK | 112 |
| Query_10004 | 81 | SRVEAEDVGVYYCSQGIHFPRIFGQGTKVEIK | 112 |

Query_10001: 7G6VL
Query_10002: h7G6VL-v1
Query_10003: h7G6VL-v2
Query_10004: 7G6VL-v3

B.

| | | | |
|---|---|---|---|
| Query_10001 | 1 | QVQLQQSGAELARPGASVKLSCKASGYSFTCYGISWVKQRTGQGLEWIGEIYPRSTNITYNRKFKGKATLTADKSSSTAF | 80 |
| Query_10002 | 1 | QVQLVQSGAEVKKPGASVKVSCKACGYTFTDYGISWVRQAPGQGLEWMGEIYPRSTNIYYNEKFKGRVTMTRDKSSSTAY | 80 |
| Query_10003 | 1 | QVQLVQSGAEVKKPGASVKVSCKASGYSFTSYGISWVRQAPGQGLEWIGEIYPRSTNITYNREFRGKATLTADKSSSTAY | 80 |

| | | | |
|---|---|---|---|
| Query_10001 | 81 | MELRSLTSEDSAVYFCARESFYGDYAMDYWGQGASVTVSS | 121 |
| Query_10002 | 81 | MELSSLRSEDTAVYYCARESFYGDYAMDYWGQGTLVTVSS | 121 |
| Query_10003 | 81 | MELSSLRSEDTAVYYCARESFYGDYAMDYWGQGTLVTVSS | 121 |

Query_10001: 7G6VH
Query_10002: h7G6VH-v1
Query_10003: hu7G6VH-v2

Figure 1

SEQUENCE LISTING

<160> NUMBER OF SEQ ID NOS: 28

<210> SEQ ID NO 1
<211> LENGTH: 27
<212> TYPE: DNA
<213> ORGANISM: Artificial Sequence
<220> FEATURE:
<223> OTHER INFORMATION: primer KF-1-EcoRV
<220> FEATURE:
<221> NAME/KEY: misc_feature
<222> LOCATION: (10)..(10)
<223> OTHER INFORMATION: k is G or T
<220> FEATURE:
<221> NAME/KEY: misc_feature
<222> LOCATION: (13)..(13)

```
<223> OTHER INFORMATION: m is A or C
<220> FEATURE:
<221> NAME/KEY: misc_feature
<222> LOCATION: (15)..(15)
<223> OTHER INFORMATION: s is C or G
<220> FEATURE:
<221> NAME/KEY: misc_feature
<222> LOCATION: (22)..(22)
<223> OTHER INFORMATION: w is A or T

<400> SEQUENCE: 1
ggtgatatck tgmtsaccca awctcca                                                27

<210> SEQ ID NO 2
<211> LENGTH: 32
<212> TYPE: DNA
<213> ORGANISM: Artificial Sequence
<220> FEATURE:
<223> OTHER INFORMATION: primer KR-BamHI

<400> SEQUENCE: 2
gggaagatgg atccagttgg tgcagcatca gc                                          32

<210> SEQ ID NO 3
<211> LENGTH: 22
<212> TYPE: DNA
<213> ORGANISM: Artificial Sequence
<220> FEATURE:
<223> OTHER INFORMATION: primer GF-2-PstI

<400> SEQUENCE: 3
aggtsmaact gcagsagtcw gg                                                     22

<210> SEQ ID NO 4
<211> LENGTH: 38
<212> TYPE: DNA
<213> ORGANISM: Artificial Sequence
<220> FEATURE:
<223> OTHER INFORMATION: primer GR-HindIII

<400> SEQUENCE: 4
ccaggggcca gtggatagac aagcttgggt gtcgtttt                                    38

<210> SEQ ID NO 5
<211> LENGTH: 363
<212> TYPE: DNA
<213> ORGANISM: Artificial Sequence
<220> FEATURE:
<223> OTHER INFORMATION: 7G6VH

<400> SEQUENCE: 5
caggttcagc tgcagcagtc tggagctgaa ctggcgaggc ctggggcttc agtgaagctg           60
tcctgcaagg cttctggcta cagcttcaca agttatggta taagttgggt gaagcagaga          120
actggacagg gccttgagtg gatcggagag atttatccta gaagtactaa tacttactac          180
aatgagaagt tcatgggcaa ggccacactg actgcagaca aatcctccag cacagcgttc          240
atggagctcc gcagcctgac atctgaggac tctgcggtct atttctgtgc aagagaatcc          300
ttctatggtg actatggggc tatggacttc tggggtcagg gagcctcagt caccgtctcc          360
tca                                                                        363

<210> SEQ ID NO 6
<211> LENGTH: 121
<212> TYPE: PRT
<213> ORGANISM: Artificial Sequence
```

<220> FEATURE:
<223> OTHER INFORMATION: 7G6VH

<400> SEQUENCE: 6

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Ser Phe Thr Ser Tyr
            20                  25                  30

Gly Ile Ser Trp Val Lys Gln Arg Thr Gly Gln Gly Leu Glu Trp Ile
        35                  40                  45

Gly Glu Ile Tyr Pro Arg Ser Thr Asn Thr Tyr Tyr Asn Glu Lys Phe
    50                  55                  60

Met Gly Lys Ala Thr Leu Thr Ala Asp Lys Ser Ser Ser Thr Ala Phe
65                  70                  75                  80

Met Glu Leu Arg Ser Leu Thr Ser Glu Asp Ser Ala Val Tyr Phe Cys
                85                  90                  95

Ala Arg Glu Ser Phe Tyr Gly Asp Tyr Gly Ala Met Asp Phe Trp Gly
            100                 105                 110

Gln Gly Ala Ser Val Thr Val Ser Ser
        115                 120

<210> SEQ ID NO 7
<211> LENGTH: 5
<212> TYPE: PRT
<213> ORGANISM: Artificial Sequence
<220> FEATURE:
<223> OTHER INFORMATION: 7G6 VH CDR1 KABAT

<400> SEQUENCE: 7

Ser Tyr Gly Ile Ser
1               5

<210> SEQ ID NO 8
<211> LENGTH: 17
<212> TYPE: PRT
<213> ORGANISM: Artificial Sequence
<220> FEATURE:
<223> OTHER INFORMATION: 7G6 VH CDR2 KABAT

<400> SEQUENCE: 8

Glu Ile Tyr Pro Arg Ser Thr Asn Thr Tyr Tyr Asn Glu Lys Phe Met
1               5                   10                  15

Gly

<210> SEQ ID NO 9
<211> LENGTH: 12
<212> TYPE: PRT
<213> ORGANISM: Artificial Sequence
<220> FEATURE:
<223> OTHER INFORMATION: 7G6 VH CDR3 KABAT

<400> SEQUENCE: 9

Glu Ser Phe Tyr Gly Asp Tyr Gly Ala Met Asp Phe
1               5                   10

<210> SEQ ID NO 10
<211> LENGTH: 290
<212> TYPE: DNA
<213> ORGANISM: Artificial Sequence
<220> FEATURE:
<223> OTHER INFORMATION: 7G6VL

<400> SEQUENCE: 10
gatatcgtgc tgacccaatc tccactcact ttgtcggtta ccattggaca accagcctcc          60
atcttttgca agtcaagtca gagcctctta gaaagtgatg gaaagacata tttgaattgg         120
ttgttgcaga ggccaggcca gtctccaaag cgccttatct atctggtgtc taaactggac         180
tctggagtcc ctgacaggtt cactggcagt ggatcaggga cagatttcac actgaagatc         240
agcagagtgg aggctgagga tttgggagtt tattattgct gccaaggtac                    290

<210> SEQ ID NO 11
<211> LENGTH: 112
<212> TYPE: PRT
<213> ORGANISM: Artificial Sequence
<220> FEATURE:
<223> OTHER INFORMATION: 7G6VL

<400> SEQUENCE: 11

Asp Ile Val Leu Thr Gln Ser Pro Leu Thr Leu Ser Val Thr Ile Gly
1               5                   10                  15

Gln Pro Ala Ser Ile Phe Cys Lys Ser Ser Gln Ser Leu Leu Glu Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Cys Gln Gly
                85                  90                  95

Thr His Phe Pro Arg Thr Phe Gly Gly Gly Thr Lys Leu Glu Ile Lys
            100                 105                 110

<210> SEQ ID NO 12
<211> LENGTH: 16
<212> TYPE: PRT
<213> ORGANISM: Artificial Sequence
<220> FEATURE:
<223> OTHER INFORMATION: 7G6 VL CDR1 KABAT

<400> SEQUENCE: 12

Lys Ser Ser Gln Ser Leu Leu Glu Ser Asp Gly Lys Thr Tyr Leu Asn
1               5                   10                  15

<210> SEQ ID NO 13
<211> LENGTH: 7
<212> TYPE: PRT
<213> ORGANISM: Artificial Sequence
<220> FEATURE:
<223> OTHER INFORMATION: 7G6 VL CDR2 KABAT

<400> SEQUENCE: 13

Leu Val Ser Lys Leu Asp Ser
1               5

<210> SEQ ID NO 14
<211> LENGTH: 8
<212> TYPE: PRT
<213> ORGANISM: Artificial Sequence
<220> FEATURE:
<223> OTHER INFORMATION: 7G6 VL CDR3 KABAT

<400> SEQUENCE: 14

```
Gln Gly Thr His Phe Pro Arg Thr
1               5
```

<210> SEQ ID NO 15
<211> LENGTH: 121
<212> TYPE: PRT
<213> ORGANISM: Artificial Sequence
<220> FEATURE:
<223> OTHER INFORMATION: h7G6VH-v1

<400> SEQUENCE: 15

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Glu Ile Tyr Pro Arg Ser Thr Asn Thr Tyr Tyr Asn Glu Lys Phe
    50                  55                  60

Met Gly Arg Val Thr Met Thr Arg Asp Lys Ser Ser Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Glu Ser Phe Tyr Gly Asp Tyr Gly Ala Met Asp Phe Trp Gly
            100                 105                 110

Gln Gly Thr Leu Val Thr Val Ser Ser
        115                 120
```

<210> SEQ ID NO 16
<211> LENGTH: 121
<212> TYPE: PRT
<213> ORGANISM: Artificial Sequence
<220> FEATURE:
<223> OTHER INFORMATION: hu7G6VH-v2

<400> SEQUENCE: 16

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Gly Ile Ser Trp Val Lys Gln Ala Pro Gly Gln Gly Leu Glu Trp Ile
        35                  40                  45

Gly Glu Ile Tyr Pro Arg Ser Thr Asn Thr Tyr Tyr Asn Glu Lys Phe
    50                  55                  60

Met Gly Lys Ala Thr Leu Thr Ala Asp Lys Ser Ser Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Glu Ser Phe Tyr Gly Asp Tyr Gly Ala Met Asp Phe Trp Gly
            100                 105                 110

Gln Gly Thr Leu Val Thr Val Ser Ser
        115                 120
```

<210> SEQ ID NO 17
<211> LENGTH: 112
<212> TYPE: PRT
<213> ORGANISM: Artificial Sequence -continued

```
<220> FEATURE:
<223> OTHER INFORMATION: h7G6VL-v1

<400> SEQUENCE: 17

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Glu Ser
            20                  25                  30

Asp Gly Lys Thr Tyr Leu Asn Trp Tyr Leu Gln Lys Pro Gly Gln Ser
        35                  40                  45

Pro Gln Leu Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Thr Phe Gly Gln Gly Thr Lys Val Glu Ile Lys
            100                 105                 110

<210> SEQ ID NO 18
<211> LENGTH: 112
<212> TYPE: PRT
<213> ORGANISM: Artificial Sequence
<220> FEATURE:
<223> OTHER INFORMATION: h7G6VL-v2

<400> SEQUENCE: 18

Asp Ile Val Leu Thr Gln Ser Pro Leu Ser Leu Pro Val Thr Pro Gly
1               5                   10                  15

Glu Pro Ala Ser Ile Phe Cys Lys Ser Ser Gln Ser Leu Leu Glu Ser
            20                  25                  30

Asp Gly Lys Thr Tyr Leu Asn Trp Leu Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Gly
                85                  90                  95

Thr His Phe Pro Arg Thr Phe Gly Gln Gly Thr Lys Val Glu Ile Lys
            100                 105                 110

<210> SEQ ID NO 19
<211> LENGTH: 112
<212> TYPE: PRT
<213> ORGANISM: Artificial Sequence
<220> FEATURE:
<223> OTHER INFORMATION: 7G6VL-v3

<400> SEQUENCE: 19

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Glu Ser
            20                  25                  30

Asp Gly Lys Thr Tyr Leu Asn Trp Tyr Leu Gln Lys Pro Gly Gln Ser
        35                  40                  45

Pro Gln Leu Leu Ile Tyr Leu Val Ser Lys Leu Asp Ser Gly Val Pro
    50                  55                  60
```

-continued

```
Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Gly
                85                  90                  95

Thr His Phe Pro Arg Thr Phe Gly Gln Gly Thr Lys Val Glu Ile Lys
                100                 105                 110

<210> SEQ ID NO 20
<211> LENGTH: 327
<212> TYPE: PRT
<213> ORGANISM: Artificial Sequence
<220> FEATURE:
<223> OTHER INFORMATION: mutant human IgG4-Fc region

<400> SEQUENCE: 20

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320
```

-continued

Leu Ser Leu Ser Leu Gly Lys
            325

<210> SEQ ID NO 21
<211> LENGTH: 448
<212> TYPE: PRT
<213> ORGANISM: Artificial Sequence
<220> FEATURE:
<223> OTHER INFORMATION: h7G6 antibody heavy chain 1

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Glu Ile Tyr Pro Arg Ser Thr Asn Thr Tyr Tyr Asn Glu Lys Phe
    50                  55                  60

Met Gly Arg Val Thr Met Thr Arg Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Phe Tyr Gly Asp Tyr Gly Ala Met Asp Phe Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

-continued

```
Pro Pro Ser Gln Glu Glu Met Thr Lys Asn Gln Val Ser Leu Thr Cys
        355                 360             365

Leu Val Lys Gly Phe Tyr Pro Ser Asp Ile Ala Val Glu Trp Glu Ser
        370             375             380

Asn Gly Gln Pro Glu Asn Asn Tyr Lys Thr Thr Pro Pro Val Leu Asp
385                 390             395                 400

Ser Asp Gly Ser Phe Phe Leu Tyr Ser Arg Leu Thr Val Asp Lys Ser
            405             410             415

Arg Trp Gln Glu Gly Asn Val Phe Ser Cys Ser Val Met His Glu Ala
        420             425             430

Leu His Asn His Tyr Thr Gln Lys Ser Leu Ser Leu Ser Leu Gly Lys
        435             440             445

<210> SEQ ID NO 22
<211> LENGTH: 448
<212> TYPE: PRT
<213> ORGANISM: Artificial Sequence
<220> FEATURE:
<223> OTHER INFORMATION: h7G6 antibody heavy chain 2

<400> SEQUENCE: 22

Gln Val Gln Leu Val Gln Ser Gly Ala Glu Val Lys Lys Pro Gly Ala
1                 5                  10                  15

Ser Val Lys Val Ser Cys Lys Ala Ser Gly Tyr Ser Phe Thr Ser Tyr
            20                  25                  30

Gly Ile Ser Trp Val Lys Gln Ala Pro Gly Gln Gly Leu Glu Trp Ile
        35                  40                  45

Gly Glu Ile Tyr Pro Arg Ser Thr Asn Thr Tyr Tyr Asn Glu Lys Phe
        50                  55                  60

Met Gly Lys Ala Thr Leu Thr Ala Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Phe Tyr Gly Asp Tyr Gly Ala Met Asp Phe Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
        210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
            260                 265                 270
```

-continued

```
Glu Val Gln Phe Asn Trp Tyr Val Asp Gly Val Glu Val His Asn Ala
        275             280             285

Lys Thr Lys Pro Arg Glu Glu Gln Phe Asn Ser Thr Tyr Arg Val Val
        290             295             300

Ser Val Leu Thr Val Leu His Gln Asp Trp Leu Asn Gly Lys Glu Tyr
305             310             315             320

Lys Cys Lys Val Ser Asn Lys Gly Leu Pro Ser Ser Ile Glu Lys Thr
            325             330             335

Ile Ser Lys Ala Lys Gly Gln Pro Arg Glu Pro Gln Val Tyr Thr Leu
            340             345             350

Pro Pro Ser Gln Glu Glu Met Thr Lys Asn Gln Val Ser Leu Thr Cys
            355             360             365

Leu Val Lys Gly Phe Tyr Pro Ser Asp Ile Ala Val Glu Trp Glu Ser
        370             375             380

Asn Gly Gln Pro Glu Asn Asn Tyr Lys Thr Thr Pro Pro Val Leu Asp
385             390             395             400

Ser Asp Gly Ser Phe Phe Leu Tyr Ser Arg Leu Thr Val Asp Lys Ser
            405             410             415

Arg Trp Gln Glu Gly Asn Val Phe Ser Cys Ser Val Met His Glu Ala
            420             425             430

Leu His Asn His Tyr Thr Gln Lys Ser Leu Ser Leu Ser Leu Gly Lys
        435             440             445
```

```
<210> SEQ ID NO 23
<211> LENGTH: 106
<212> TYPE: PRT
<213> ORGANISM: Artificial Sequence
<220> FEATURE:
<223> OTHER INFORMATION: Ig kappa constant region

<400> SEQUENCE: 23

Thr Val Ala Ala Pro Ser Val Phe Ile Phe Pro Pro Ser Asp Glu Gln
1               5               10              15

Leu Lys Ser Gly Thr Ala Ser Val Val Cys Leu Leu Asn Asn Phe Tyr
            20              25              30

Pro Arg Glu Ala Lys Val Gln Trp Lys Val Asp Asn Ala Leu Gln Ser
        35              40              45

Gly Asn Ser Gln Glu Ser Val Thr Glu Gln Asp Ser Lys Asp Ser Thr
    50              55              60

Tyr Ser Leu Ser Ser Thr Leu Thr Leu Ser Lys Ala Asp Tyr Glu Lys
65              70              75              80

His Lys Val Tyr Ala Cys Glu Val Thr His Gln Gly Leu Ser Ser Pro
            85              90              95

Val Thr Lys Ser Phe Asn Arg Gly Glu Cys
            100             105
```

```
<210> SEQ ID NO 24
<211> LENGTH: 219
<212> TYPE: PRT
<213> ORGANISM: Artificial Sequence
<220> FEATURE:
<223> OTHER INFORMATION: h7G6 light chain 1

<400> SEQUENCE: 24

Asp Ile Val Met Thr Gln Ser Pro Leu Ser Leu Pro Val Thr Pro Gly
1               5               10              15

Glu Pro Ala Ser Ile Ser Cys Lys Ser Ser Gln Ser Leu Leu Glu Ser
            20              25              30
```

```
Asp Gly Lys Thr Tyr Leu Asn Trp Tyr Leu Gln Lys Pro Gly Gln Ser
        35                  40                  45

Pro Gln Leu Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Thr Phe Gly Gln Gly Thr Lys Val Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
    210                 215
```

```
<210> SEQ ID NO 25
<211> LENGTH: 219
<212> TYPE: PRT
<213> ORGANISM: Artificial Sequence
<220> FEATURE:
<223> OTHER INFORMATION: h7G6 light chain 2

<400> SEQUENCE: 25
```

```
Asp Ile Val Leu Thr Gln Ser Pro Leu Ser Leu Pro Val Thr Pro Gly
1               5                   10                  15

Glu Pro Ala Ser Ile Phe Cys Lys Ser Ser Gln Ser Leu Leu Glu Ser
                20                  25                  30

Asp Gly Lys Thr Tyr Leu Asn Trp Leu Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Gly
                85                  90                  95

Thr His Phe Pro Arg Thr Phe Gly Gln Gly Thr Lys Val Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175
```

```
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 26
<211> LENGTH: 219
<212> TYPE: PRT
<213> ORGANISM: Artificial Sequence
<220> FEATURE:
<223> OTHER INFORMATION: h7G6 light chain 3

<400> SEQUENCE: 26

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Glu Ser
            20                  25                  30

Asp Gly Lys Thr Tyr Leu Asn Trp Tyr Leu Gln Lys Pro Gly Gln Ser
        35                  40                  45

Pro Gln Leu Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Gly
                85                  90                  95

Thr His Phe Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 27
<211> LENGTH: 160
<212> TYPE: PRT
<213> ORGANISM: Artificial Sequence
<220> FEATURE:
<223> OTHER INFORMATION: hTFPI-K1K2

<400> SEQUENCE: 27

Asp Ser Glu Glu Asp Glu Glu His Thr Ile Ile Thr Asp Thr Glu Leu
1               5                   10                  15

Pro Pro Leu Lys Leu Met His Ser Phe Cys Ala Phe Lys Ala Asp Asp
            20                  25                  30
```

Gly Pro Cys Lys Ala Ile Met Lys Arg Phe Phe Phe Asn Ile Phe Thr
        35                  40                  45

Arg Gln Cys Glu Glu Phe Ile Tyr Gly Gly Cys Glu Gly Asn Gln Asn
    50                  55                  60

Arg Phe Glu Ser Leu Glu Glu Cys Lys Lys Met Cys Thr Arg Asp Asn
65                  70                  75                  80

Ala Asn Arg Ile Ile Lys Thr Thr Leu Gln Gln Glu Lys Pro Asp Phe
                85                  90                  95

Cys Phe Leu Glu Glu Asp Pro Gly Ile Cys Arg Gly Tyr Ile Thr Arg
                100                 105                 110

Tyr Phe Tyr Asn Asn Gln Thr Lys Gln Cys Glu Arg Phe Lys Tyr Gly
                115                 120                 125

Gly Cys Leu Gly Asn Met Asn Asn Phe Glu Thr Leu Glu Glu Cys Lys
        130                 135                 140

Asn Ile Cys Glu Asp Gly Pro Asn Gly Phe Gln Val Asp Asn Tyr Gly
145                 150                 155                 160

<210> SEQ ID NO 28
<211> LENGTH: 304
<212> TYPE: PRT
<213> ORGANISM: Homo sapiens

<400> SEQUENCE: 28

Met Ile Tyr Thr Met Lys Lys Val His Ala Leu Trp Ala Ser Val Cys
1               5                   10                  15

Leu Leu Leu Asn Leu Ala Pro Ala Pro Leu Asn Ala Asp Ser Glu Glu
                20                  25                  30

Asp Glu Glu His Thr Ile Ile Thr Asp Thr Glu Leu Pro Pro Leu Lys
            35                  40                  45

Leu Met His Ser Phe Cys Ala Phe Lys Ala Asp Asp Gly Pro Cys Lys
    50                  55                  60

Ala Ile Met Lys Arg Phe Phe Phe Asn Ile Phe Thr Arg Gln Cys Glu
65                  70                  75                  80

Glu Phe Ile Tyr Gly Gly Cys Glu Gly Asn Gln Asn Arg Phe Glu Ser
                85                  90                  95

Leu Glu Glu Cys Lys Lys Met Cys Thr Arg Asp Asn Ala Asn Arg Ile
                100                 105                 110

Ile Lys Thr Thr Leu Gln Gln Glu Lys Pro Asp Phe Cys Phe Leu Glu
        115                 120                 125

Glu Asp Pro Gly Ile Cys Arg Gly Tyr Ile Thr Arg Tyr Phe Tyr Asn
    130                 135                 140

Asn Gln Thr Lys Gln Cys Glu Arg Phe Lys Tyr Gly Gly Cys Leu Gly
145                 150                 155                 160

Asn Met Asn Asn Phe Glu Thr Leu Glu Glu Cys Lys Asn Ile Cys Glu
                165                 170                 175

Asp Gly Pro Asn Gly Phe Gln Val Asp Asn Tyr Gly Thr Gln Leu Asn
                180                 185                 190

Ala Val Asn Asn Ser Leu Thr Pro Gln Ser Thr Lys Val Pro Ser Leu
        195                 200                 205

Phe Glu Phe His Gly Pro Ser Trp Cys Leu Thr Pro Ala Asp Arg Gly
    210                 215                 220

Leu Cys Arg Ala Asn Glu Asn Arg Phe Tyr Tyr Asn Ser Val Ile Gly
225                 230                 235                 240

-continued

```
Lys Cys Arg Pro Phe Lys Tyr Ser Gly Cys Gly Gly Asn Glu Asn Asn
                245             250             255

Phe Thr Ser Lys Gln Glu Cys Leu Arg Ala Cys Lys Lys Gly Phe Ile
            260             265             270

Gln Arg Ile Ser Lys Gly Gly Leu Ile Lys Thr Lys Arg Lys Arg Lys
        275             280             285

Lys Gln Arg Val Lys Ile Ala Tyr Glu Glu Ile Phe Val Lys Asn Met
    290             295             300
```

MONOCLONAL ANTIBODY WHICH TARGETS TFPI

TECHNICAL FIELD

The invention relates to the field of biomedicine. Specifically, the invention discloses a monoclonal antibody against tissue factor pathway inhibitor (TFPI) or antigen-binding fragment thereof, as well as medical uses thereof.

BACKGROUND ART

Blood coagulation is a process by which blood forms a stable clot to stop bleeding. This process involves many zymogens and cofactors (or "coagulation factors") circulating in blood. Those zymogens and cofactors interact through several ways to convert them into activated forms sequentially or simultaneously. Finally, the process leads to activation of prothrombin to thrombin by activated factor X (FXa) in the presence of factor Va, ionized calcium, and platelets. The activated thrombin then induces platelet aggregation and converts fibrinogen to fibrin, which is then crosslinked by the activated factor XIII (FXIIIa) to form a clot.

There are two unique ways to activate factor X: the contact activation pathway (formerly known as the intrinsic pathway) and the tissue factor pathway (formerly known as the extrinsic pathway). Now it is known that the primary pathway for the initiation of blood coagulation is the tissue factor pathway.

The factor X can be activated by the tissue factor (TF) combined with the activated factor VII (FVIIa). The complex of FVIIa and its essential co-factor TF is a powerful initiator of the coagulation cascade.

The tissue factor pathway of coagulation is negatively controlled by tissue factor pathway inhibitor ("TFPI"). TFPI is a natural, FXa-dependent feedback inhibitor of FVIIa/TF complex, which belongs to the multivalent Kunitz-type serine proteinase inhibitors. Physiologically, TFPI binds to the activated factor X (FXa) to form a heterodimer complex, which then interacts with the FVIIa/TF complex to inhibit its activity, thus closing the coagulation tissue factor pathway. In principle, inhibition of TFPI activity can restore FXa and FVIIa/TF activities, thus prolonging the duration of tissue factor pathway and amplifying FXa generation. Both hemophilia A and hemophilia B lack FXa.

There is still a need in the art for pharmaceutical agents that can inhibit TFPI activity, such as TFPI-specific antibodies, to treat coagulation-related disorders.

BRIEF DESCRIPTION OF THE DRAWINGS

FIG. 1 shows the amino acid sequence alignment results of a humanized light chain and murine light chain (A), humanized heavy chain variant and murine heavy chain (B).

DETAILED DESCRIPTION OF THE INVENTION

I. Definitions

Figure 2:
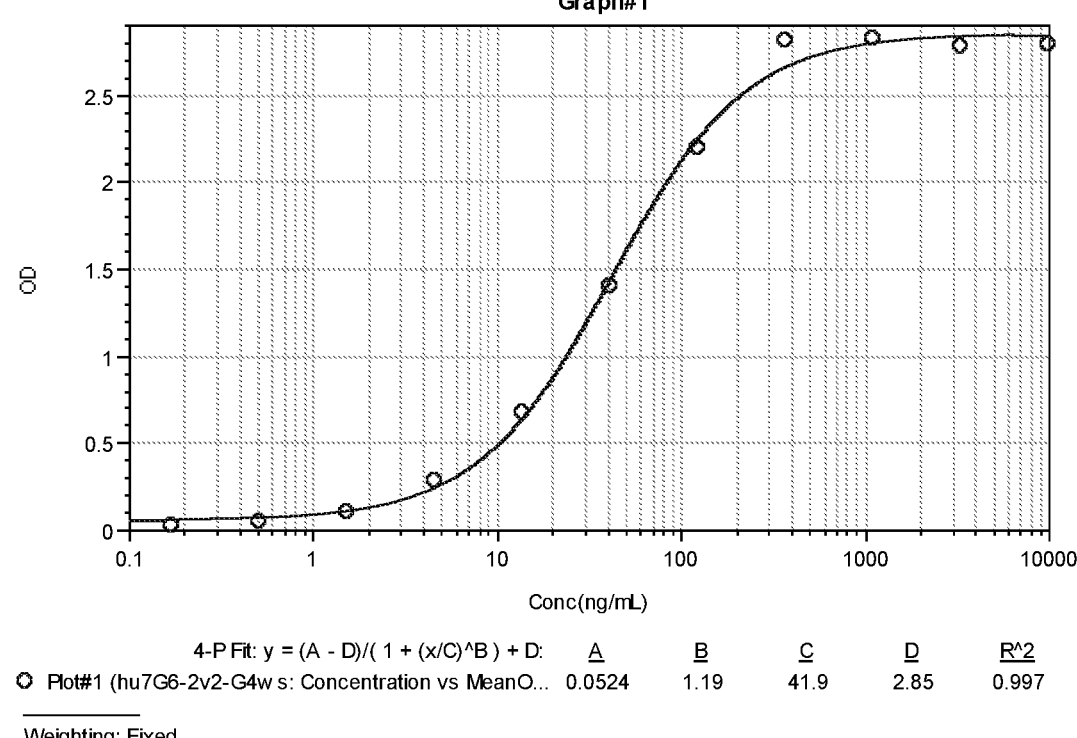
FIG. 2 shows the affinity of the humanized h7G6 antibody to hTFPI.

In the present invention, unless defined otherwise, all scientific and technical terms used herein have the same meaning as those commonly understood by those skilled in the art. In addition, the terms related to protein and nucleic acid chemistry, molecular biology, cell and tissue culture, microbiology, immunology, and laboratory operation procedures used herein are all widely used terms and routine procedures in the corresponding fields. Meanwhile, in order to better understand the present invention, definitions and explanations of related terms are provided below.

As used herein, the term "tissue factor pathway inhibitor" or "TFPI" refers to any variant, isoform and homologue of human TFPI naturally expressed by cells. Exemplary human TFPI comprises the amino acid sequence shown in SEQ ID NO: 28.

As used herein, an "antibody" refers to immunoglobulins and immunoglobulin fragments, whether natural or partially or all synthesized (e.g., recombinantly) produced, including any fragment which comprises at least part of the variable region of an immunoglobulin molecule and retains the binding specificity of the full-length immunoglobulin. Therefore, an antibody includes any protein with a binding domain homologous or substantially homologous to the antigen-binding domain of an immunoglobulin (the antibody's binding site). Antibodies include antibody fragments, such as antibody fragments of anti-tumor cells. As used herein, the term antibody therefore includes synthetic antibodies, recombinant antibodies, multispecific antibodies (e.g., bispecific antibodies), human antibodies, non-human antibodies, humanized antibodies, chimeric antibodies, intracellular antibodies, and antibody fragments, such as, but not limited to, Fab, Fab', F(ab')$_2$ and Fv fragments, disulfide-linked Fv (dsFv), Fd fragments, Fd' fragments, single-chain Fab (scFab) fragments, diabodies, anti-idiotype (anti-Id) antibodies, or antigen-binding fragments of any antibody above. The antibodies provided herein include any immunoglobulin class (for example, IgG, IgM, IgD, IgE, IgA and IgY), members of any class (for example, IgG1, IgG2, IgG3, IgG4, IgA1, and IgA2) or any subclass (for example, IgG2a and IgG2b).

As used herein, the "antibody fragment" or "antigen-binding fragment" of an antibody refers to any part of a full-length antibody, which is less than the full length, but comprises at least part of the variable region of the antibody that binds to the antigen (for example, one or more CDRs and/or one or more antigen-binding sites), and thus retains the binding specificity and at least part of the specific binding capability of the full-length antibody. Therefore, the antigen-binding fragment refers to an antibody fragment that comprises an antigen-binding portion that binds to an antigen to which the antibody fragment-derived antibody binds. Antibody fragments include antibody derivatives produced by the enzymatic treatment of full-length antibodies, as well as synthetically produced derivatives, such as recombinantly produced derivatives. Antibodies include antibody fragments. Examples of antibody fragments include, but are not limited to, Fab, Fab', F(ab')$_2$, single chain Fv (scFv), Fv, dsFv, a diabody, Fd and Fd fragments and other fragments, including modified fragments (See, for example, Methods in Molecular Biology, Vol 207: Recombinant Antibodies for Cancer Therapy Methods and Protocols (2003); Chapter 1; p 3-25, Kipriyanov). The fragments may include multiple chains linked together, for example, by disulfide bonds and/or peptide linkers. Antibody fragments generally comprise at least or about 50 amino acids, and typically at least or about 200 amino acids. The antigen-binding fragment includes any antibody fragment that is inserted into the antibody framework (for example, by replacing the corresponding region) to obtain an antibody that immunospecifically binds to the antigen (i.e., manifests at least or at least about $10^7$-$10^8$ M$^{-1}$ Ka).

As used herein, a "monoclonal antibody" refers to the population of the same antibody, which means that each individual antibody molecule in the monoclonal antibody population is the same as other antibody molecules. This characteristic is opposite to that of the polyclonal population of antibodies, which contains antibodies with a wide variety of sequences. monoclonal antibodies can be prepared by many well-known methods (Smith et al. (2004) *J. clin. pathol.* 57, 912-917; and Nelson et al., *J clin pathol* (2000), 53, 111-117). For example, monoclonal antibodies can be prepared by immortalized B cells, such as by fusing with myeloma cells to produce hybridoma cell lines or by infecting B cells with viruses such as EBV. Recombinant technologies can also be used to prepare antibodies from the cloned population of host cells in vitro by transforming the host cells with plasmids carrying artificial sequences of nucleotides encoding the antibodies.

As used herein, the term "hybridoma" or "hybridoma cell" refers to a cell or cell line (usually, myeloma or lymphoma cells) produced by fusing lymphocytes producing antibodies with cancer cells not producing antibodies. As known by those skilled in the art, hybridomas can proliferate and continuously supply specific monoclonal antibodies. Methods for producing hybridomas are known in the art (see, for example, Harlow & Lane, 1988). When the term "hybridoma" or "hybridoma cell" is mentioned, it also includes subclones and progeny cells of hybridomas.

As used herein, a "conventional antibody" refers to an antibody comprising two heavy chains (which can be labeled as H and H') and two light chains (which can be labeled as L and L') and two antigen-binding sites, in which each heavy chain can be a full-length immunoglobulin heavy chain or any functional region thereof that retains antigen-binding ability (for example, heavy chains include, but are not limited to a $V_H$ chain, $V_H$-$C_H1$ chain, and $V_H$-$C_H1$-$C_H2$-$C_H3$ chain), and each heavy chain can be a full-length light chain or any functional region thereof (for example, light chains include, but are not limited to a $V_L$ chain and $V_L$-$C_L$ chain). Each heavy chain (H and H') is paired with one light chain (L and L', respectively).

As used herein, a full-length antibody is one comprised of two full-length heavy chains (for example, $V_H$-$C_H1$-$C_H2$-$C_H3$ or $V_H$-$C_H1$-$C_H2$-$C_H3$-$C_H4$), two full-length light chains ($V_L$-$C_L$) and a hinge region, such as, antibodies naturally produced by antibody-secreting B cells or synthetically produced antibodies having the same domain.

As used herein, dsFv refers to Fv with engineered intermolecular disulfide bonds stabling $V_H$-$V_L$ pairs.

As used herein, Fab fragments are antibody fragments obtained by digesting a full-length immunoglobulin with papain, or for example, fragments having the same structure synthesized by recombinant methods. Fab fragments comprise one light chain (including $V_L$ and $C_L$) and another chain, which comprises the variable domain ($V_H$) and one constant domain ($C_H1$) of a heavy chain.

As used herein, F(ab')$_2$ fragments are antibody fragments obtained by digesting the immunoglobulin with pepsin at pH 4.0-4.5, or for example, fragments having the same structure synthesized by recombinant methods. An F(ab')$_2$ fragment basically comprises two Fab fragments, in which each heavy chain portion comprises several additional amino acids, including cysteine forming disulfide bonds linking the two fragments.

As used herein, a Fab' fragment is a fragment comprising half of the F(ab')$_2$ fragment (a heavy chain and light chain).

As used herein, a scFv fragment refers to an antibody fragment comprising a variable light chain ($V_L$) and a variable heavy chain ($V_H$) covalently linked by a polypeptide linker in any order. The length of the linker is such that the two variable domains can be bridged basically without interference. An exemplary linker is a (Gly-Ser)$_n$ residue dispersed with a few of Glu or Lys residues favorable in solubility.

The term "chimeric antibody" refers to such an antibody, in which the variable region sequence is derived from one species and the constant region sequence is derived from another species, such as the antibody in which the variable region sequence is derived from a mouse antibody and the constant region sequence is derived from a human antibody.

A "humanized antibody" refers to a non-human (e.g., mouse) antibody form, which is a chimeric immunoglobulin, immunoglobulin chain or fragment thereof (e.g., Fv, Fab, Fab', F(ab')$_2$ or other antigen-binding subsequences of the antibody) and comprises a minimal sequence derived from a non-human immunoglobulin. Preferably, the humanized antibody is a human immunoglobulin (recipient's antibody), in which residues from the complementarity determining region (CDR) of the recipient's antibody are replaced by residues from the CDR of a non-human species (donor's antibody), such as a mouse, rat or rabbit, which has the desired specificity, affinity, and capability.

In addition, in humanization, it is also possible to mutate amino acid residues in CDR1, CDR2 and/or CDR3 regions of the VH and/or VL, thereby improving one or more binding characteristics (such as affinity) of antibodies. For example, mutation can be introduced by PCR-mediated mutation, and its influence on the binding or other functional characteristics of the antibody can be evaluated by in vitro or in vivo assays described herein. Usually, conservative mutations are introduced. Such mutations can be amino acid substitutions, additions, or deletions. In addition, no more than one or two mutations are generally found in CDRs. Therefore, the humanized antibody according to the present invention also covers antibodies with 1 or 2 amino acid mutations in CDRs.

As used herein, the term "epitope" refers to any antigenic determinant on the antigen to which the complementary site of an antibody binds. Generally, epitopes comprise chemically active surface structures of molecules, such as amino acids or sugar side chains, and usually have specific three-dimensional structure characteristics and specific charge characteristics.

As used herein, a variable domain or variable region is a specific Ig domain of a heavy or light chain of an antibody, which comprises amino acid sequences that vary between different antibodies. Each light chain and heavy chain have a variable region domain $V_L$ and $V_H$, respectively. The variable domain offers antigen specificity and is therefore responsible for antigen recognition. Each variable region comprises a CDR, which is a portion of an antigen-binding site domain, and a framework region (FR).

As used herein, the "antigen-binding domain" and "antigen-binding site" are used synonymously to refer to the domains in antibodies that recognize antigens and physically interact with the same. The natural conventional full-length antibody molecule has two conventional antigen-binding sites, each comprising a heavy chain variable region portion and light chain variable region portion. Conventional antigen-binding sites comprise a loop connecting anti-parallel beta chains in the variable domain. The antigen-binding site may comprise other portions of the variable region domain. Each conventional antigen-binding site comprises 3 hypervariable regions from a heavy chain and 3 hypervariable regions from a light chain. The hypervariable region is also known as the complementarity determining region (CDR).

As used herein, the terms "hypervariable region", "HV", "complementarity determining region", "CDR" and "antibody CDR" are used interchangeably to refer to one of multiple portions in each variable region that together form the antigen-binding sites of an antibody. Each variable domain comprises 3 CDRs, designated as CDR1, CDR2 and CDR3. For example, the light chain variable domain comprises 3 CDRs, designated as VL CDR1, VL CDR2 and VL CDR3; the heavy chain variable domain comprises 3 CDRs, designated as VH CDR1, VH CDR2 and VH CDR3. The 3 CDRs in the variable region are discontinuous along the linear amino acid sequences, but close to each other in the folded polypeptide. CDR is located in the loop connecting the β-folded parallel chain in the variable domain.

As described herein, as known by those skilled in the art, CDR can be defined based on the Kabat or Chothia numbering system (see, for example, Kabat, E. A. et al. (1991) Sequences of Proteins of Immunological Interest, Fifth Edition, U.S. Department of Health and Human Services, NIH Publication No. 91-3242, He Chothia, C. et al. (1987) J. mol. Biol. 196: 901-917). Alternative methods of numbering amino acid residues of CDR are also known in the art. For example, AbM CDR represents the compromise between Kabat hypervariable region and Chothia structural loop, and is used in the antibody modeling software Oxford Molecular's AbM. The "Contact" CDR is based on the analysis of the crystal structure of the available complex. The residues of CDR from each method are described as follows:

| Loop | Kabat | AbM | Chothia | Contact |
|---|---|---|---|---|
| LCDR1 | L24-L34 | L24-L34 | L26-L32 | L30-L36 |
| LCDR2 | L50-L56 | L50-L56 | L50-L52 | L46-L55 |
| LCDR3 | L89-L97 | L89-L97 | L91-L96 | L89-L96 |
| HCDR1 (Kabat numbering) | H31-H35B | H26-H35B | H26-H32 | H30-H35B |
| HCDR1 (Chothia numbering) | H31-H35 | H26-H35 | H26-H32 | H30-H35 |
| HCDR2 | H50-H65 | H50-H58 | H53-H55 | H47-H58 |
| HCDR3 | H95-H102 | H95-H102 | H96-H101 | H93-H101 |

However, it should be noted that, as well known in the art, the total number of amino acid residues in each CDR may be different and may not correspond to the total number of amino acid residues indicated by the Kabat numbering (that is, one or more positions according to the Kabat numbering system may not be occupied in the actual sequence, or the actual sequence may comprise more amino acid residues than allowed by the Kabat numbering). This means that, in general, the numbering according to Kabat may or may not correspond to the actual numbering of amino acid residues in the actual sequence. For example, CDRs can include extended CDRs, such as 24-36 or 24-34 (LCDR1), 46-56 or 50-56 (LCDR2) and 89-97 or 89-96 (LCDR3) in the VL; 26-35 (HCDR1), 50-65 or 49-65 (HCDR2) and 93-102, 94-102 or 95-102 (HCDR3) in the VH.

As used herein, the Framework region (FR) is the domain in the antibody variable region domains within the beta fold; in terms of amino acid sequence, FR regions are relatively more conservative than hypervariable regions.

As used herein, "constant region" domains are domains in the heavy chain or light chain of an antibody, which comprise amino acid sequences that are relatively more conservative than that of the variable domains. In conventional full-length antibody molecules, each light chain has a single light chain constant region ($C_L$) domain, whereas each heavy chain comprises one or more heavy chain constant region ($C_H$) domains, including $C_H1$, $C_H2$, $C_H3$, and $C_H4$. The full-length IgA, IgD and IgG isoforms comprise $C_H1$, $C_H2$, $C_H3$, and a hinge region, whereas IgE and IgM comprise $C_H1$, $C_H2$, $C_H3$, and $C_H4$. $C_H1$ and $C_L$ domains extend the Fab arms of the antibody molecule, thus facilitating the interaction with the antigen and rotating the antibody arms. The antibody constant region can serve effector functions, such as, but not limited to eliminating antigens, pathogens and toxins specifically bound by the antibody, for example, by interacting with various cells, biomolecules, and tissues.

As used herein, "specific binding" or "immuno-specific binding" of an antibody or antigen-binding fragments thereof can be used interchangeably herein, and refers to the capability of the antibody or antigen-binding fragments to form one or more non-covalent bonds with the same antigen through the noncovalent interaction between the antibody and the antibody-binding sites of the antigen. The antigen may be an isolated antigen or present in tumor cells. Generally, the antibody that immuno-specifically (or specifically) binds to an antigen binds to the antigen with an affinity constant Ka of about $1\times10^7$ M$^{-1}$ or $1\times10^8$ M$^{-1}$ or more (or a dissociation constant $K_d$ of $1\times10^{-7}$ M or $1\times10^{-8}$ or less). The affinity constant can be determined by standard kinetic methods of the antibody reaction, such as immunoassay and surface plasmon resonance (SPR) (Rich and Myzka (2000) Curr. Opin. Biotechnology 11: 54; Englebienne (1998) Analyst. 123: 1599), isothermal titration calorimetry (ITC) or other kinetic interaction assays known in the art (See, for example, Paul, ed., Fundamental Immunology, 2nd ed., Raven Press, New York, pages 332-336 (1989)). Instruments and methods for real-time detecting and monitoring the binding rate are known and commercially available (See, BiaCore 2000, Biacore A B, Upsala, Sweden and GE Healthcare Life Sciences; Malmqvist (2000) Biochem. Soc. Trans. 27:335).

As used herein, the term "competition" with respect to antibodies means that a first antibody or antigen-binding fragment thereof binds to an epitope in a manner similar enough to a second antibody or antigen-binding fragment thereof, whereby the binding result of the first antibody to its associated epitope is detectably reduced in the presence of the second antibody compared with the absence of the second antibody. Alternatively, in the case that the binding of the second antibody to its epitope is also detectably reduced in the presence of the first antibody, this may but need not be the case. That is, the first antibody may inhibit the binding of the second antibody to its epitope without inhibiting the binding of the first antibody to its respective epitope by the second antibody. However, in the case that each antibody detectably inhibits the binding of another antibody to its associated epitope or ligand, whether at the same, higher or lower degree, the antibodies are said to "cross-compete" with each other to bind their respective epitopes. Competitive and cross-competitive antibodies are all covered by the present invention. Regardless of the mechanism by which this competition or cross-competition occurs (for example, steric hindrance, conformational change or binding of common epitopes or fragment thereof), those skilled in the art will realize that this competitive and/or cross-competitive antibody is covered by the present invention and can be used in the method disclosed by the present invention based on the teaching provided by the present invention.

As used herein, a "polypeptide" refers to two or more amino acids covalently linked. The terms "polypeptide" and "protein" are used interchangeably herein.

An "isolated protein", "isolated polypeptide" or "isolated antibody" means that the protein, polypeptide or antibody (1) is not associated with naturally related components accompanied in its natural state, (2) does not contain other proteins from the same species, (3) is expressed by cells from different species, or (4) does not occur in nature. Therefore, chemically synthesized polypeptides or polypeptides synthesized in a cell system, which is different from nature-derived cells of polypeptides, will be "separated" from their naturally related components. Proteins can also be separated to be substantially free of naturally related components, that is, by using the protein purification technology well known in the art.

Suitable conservative amino acid substitutions in peptides or proteins are known to those skilled in the art, and can generally be carried out without changing the biological activity of the resultant molecules. Generally, those skilled in the art will realize that the substitution of a single amino acid in the nonessential region of a polypeptide does not substantially change the biological activity (See, for example, Watson et al., *Molecular Biology of the Gene*, 4th Edition, 1987, The Benjamin/Cummings Pub. co., p. 224).

As used herein, the terms "polynucleotide" and "nucleic acid molecule" refer to oligomers or polymers comprising at least two nucleotides or nucleotide derivatives linked together, including deoxyribonucleic acid (DNA) and ribonucleic acid (RNA), which are linked together typically by phosphodiester bonds.

As used herein, an isolated nucleic acid molecule is such a nucleic acid molecule that is separated from other nucleic acid molecules existing in the natural source of the nucleic acid molecule. "Isolated" nucleic acid molecules such as cDNA molecules can be substantially free of other cell substances or culture media when prepared by recombinant technology, or substantially free of chemical precursors or other chemical components in chemical synthesis. Exemplary isolated nucleic acid molecules provided herein include isolated nucleic acid molecules encoding the antibodies or antigen-binding fragments provided herein.

Sequence "identity" have art-established meanings, and the percentage of sequence identity between two nucleic acid or polypeptide molecules or regions can be calculated by using the published technologies. Sequence identity can be measured along the entire length of the polynucleotide or polypeptide or along the region of the molecule. (See, for example, Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). Although there are many methods to measure the identity between two polynucleotides or polypeptides, the term "identity" is well known to technicians (Carrillo, H. & Lipman, D., *SIAM J Applied Math* 48:1073 (1988)).

As used herein, "operably linked" with respect to a nucleic acid sequence, region, element, or domain, means that the nucleic acid regions are functionally related to each other. For example, a promoter may be operably linked to a nucleic acid encoding a polypeptide, thus the promoter regulates or mediates transcription of the nucleic acid.

As used herein, "expression" refers to the process of producing polypeptides through transcription and translation of polynucleotides. The expression level of polypeptide can be evaluated by any method known in the art, including, for example, the method of determining the amount of polypeptides produced from host cells. Such methods may include, but are not limited to, quantification of polypeptides in the cell lysate by ELISA, Coomassie blue staining after gel electrophoresis, Lowry protein assay, and Bradford protein assay.

As used herein, a "host cell" is a cell for receiving, maintaining, replicating, and amplifying vectors. The host cell can also be used to express the polypeptide encoded by the vector. When a host cell divides, nucleic acids contained in the vector is replicated, thus amplifying the nucleic acids. The host cell may be a eukaryotic cell or prokaryotic cell. Suitable host cells include, but are not limited to, CHO cells, various COS cells, Hela cells, HEK cells, such as HEK 293 cells.

"Codon optimization" refers to a method for modifying the nucleic acid sequence to enhance the expression in the host cell of interest by replacing at least one codon of the natural sequence (for example, about or more than about 1, 2, 3, 4, 5, 10, 15, 20, 25, 50 or even more codons) with codons used more frequently or most frequently in the genes of the host cell while maintaining the natural amino acid sequence. Different species exhibit specific preference for certain codons of specific amino acids. Codon preference (the difference of codon usage among organisms) is often related to the translation efficiency of a messenger RNA (mRNA), which is considered to be dependent on the nature of translated codons and the availability of specific transfer RNA(tRNA) molecules. The advantage of tRNA selected in cells generally reflects the codons most frequently used for peptide synthesis. Therefore, genes can be custom-designed to be the optimal gene expression in a given organism based on codon optimization. A codon usage table can be easily obtained, for example, in Codon Usage Database available on www.kazusa.orjp/codon/, which can be adapted in different ways. See Nakamura Y. et al., codon usage tabulated from the international DNA sequence databases: status for the year 2000. nucl. acids Res., 28:292 (2000).

As used herein, a "vector" is a replicable nucleic acid from which one or more heterologous proteins can be expressed when the vector is transformed into a suitable host cell. The vectors include those vectors into which nucleic acids encoding polypeptides or fragments thereof can be introduced generally by restriction digestion and ligation. The vectors also include those that comprise nucleic acids encoding polypeptides. The vectors are used to introduce nucleic acids encoding polypeptides into host cells, to amplify nucleic acids or to express/display polypeptides encoded by the nucleic acids. The vectors usually remain free but can be designed to chromosomes that integrate the gene or a fraction thereof into the genome. Artificial chromosome vectors are also considered, such as yeast artificial vectors and mammalian artificial chromosomes. The selection and use of such media are well known to those skilled in the art.

As used herein, the vector also includes a "virus vector". The virus vector is an engineered virus that is operably linked to foreign genes to transfer foreign genes (as a vehicle or shuttle) into cells.

As used herein, an "expression vector" includes a vector capable of expressing DNA, which is operably linked to regulatory sequences, such as promoter regions, which can affect the expression of such DNA fragments. Such additional fragments may include promoter and terminator sequences, and optionally one or more replication origins, one or more selection markers, enhancers, polyadenylation signals, etc. The expression vectors are generally derived from plasmids or virus DNA, or may contain the elements of both. Therefore, the expression vectors refer to recombinant DNA or RNA constructs, such as plasmids, bacteriophages, recombinant viruses or other vectors, which lead to the expression of cloned DNA when introduced into appropriate host cells. Suitable expression vectors are well known to those skilled in the art, and include expression vectors that can be replicated in eukaryotic cells and/or prokaryotic cells, and expression vectors remaining free or integrated into the genome of host cells.

As used herein, "treatment" of an individual suffering from a disease or disease condition means that the symptoms of the individual are partially or completely relieved or remain unchanged after treating. Therefore, the treatment includes prevention, remedy and/or cure. Prevention means preventing potential diseases and/or preventing symptoms from worsening or disease development. Treatment also includes any antibody or antigen-binding fragments thereof provided herein and any pharmaceutical use of the compositions provided herein.

As used herein, "efficacy" means the effect caused by the treatment of individuals, which changes, usually improves or ameliorates the symptoms of the disease or disease condition, or cures the disease or disease condition.

As used herein, a "therapeutically effective amount" or "therapeutically effective dose" refers to the amount of a substance, compound, material or composition containing the compound that is at least sufficient to produce a therapeutic effect after administration to a subject. Therefore, this is an indispensable amount to prevent, cure, improve, block or partially block the symptoms of diseases or disorders.

As used herein, the term "patient" refers to a mammal, such as a human.

II. Anti-TFPI Monoclonal Antibodies

Therefore, in one aspect, the present invention provides an isolated monoclonal antibody or antigen-binding fragment thereof against TFPI, wherein the monoclonal antibody comprises a light chain variable region and a heavy chain variable region, the light chain variable region comprising:

VL CDR1, which comprises the amino acid sequence shown in SEQ ID NO: 12 or the amino acid sequence with a substitution, deletion or addition of 1 or 2 amino acid residues compared to SEQ ID NO: 12, VL CDR2, which comprises the amino acid sequence shown in SEQ ID NO: 13 or the amino acid sequence with a substitution, deletion or addition of 1 or 2 amino acid residues compared to SEQ ID NO: 13, and VL CDR3, which comprises the amino acid sequence shown in SEQ ID NO: 14 or the amino acid sequence with a substitution, deletion or addition of 1 or 2 amino acid residues compared to SEQ ID NO: 14;

the heavy chain variable region comprising:

VH CDR1, which comprises the amino acid sequence shown in SEQ ID NO: 7 or the amino acid sequence with a substitution, deletion or addition of 1 or 2 amino acid residues compared to SEQ ID NO: 7, VH CDR2, which comprises the amino acid sequence shown in SEQ ID NO: 8 or the amino acid sequence with a substitution, deletion or addition of 1 or 2 amino acid residues compared to SEQ ID NO: 8, and VH CDR3, which comprises the amino acid sequence shown in SEQ ID NO: 9 or the amino acid sequence with a substitution, deletion or addition of 1 or 2 amino acid residues compared to SEQ ID NO: 9.

In certain embodiments, wherein the monoclonal antibody comprises a light chain variable region and heavy chain variable region, the light chain variable region comprising:

VL CDR1 comprising the amino acid sequence shown in SEQ ID NO: 12,

VL CDR2 comprising the amino acid sequence shown in SEQ ID NO: 13, and

VL CDR3 comprising the amino acid sequence shown in SEQ ID NO: 14;

the heavy chain variable region comprising:

VH CDR1 comprising the amino acid sequence shown in SEQ ID NO: 7,

VH CDR2 comprising the amino acid sequence shown in SEQ ID NO: 8, and

VH CDR3 comprising the amino acid sequence shown in SEQ ID NO: 9.

In certain embodiments, the monoclonal antibody is a humanized antibody.

In certain embodiments, the light chain variable region comprises the amino acid sequence shown in SEQ ID NO:11 or an amino acid sequence having at least 80%, at least 85%, at least 90%, at least 95% or higher sequence identity to SEQ ID NO:11. In certain embodiments, the light chain variable region comprises the amino acid sequence having about 80%, about 85%, about 86%, about 87%, about 88%, about 89%, about 90%, about 91%, about 92%, about 93%, about 94%, about 95%, about 96%, about 97%, about 98%, or about 99% sequence identity to SEQ ID NO: 11.

In certain embodiments, the heavy chain variable region comprises the amino acid sequence shown in SEQ ID NO: 6 or an amino acid sequence having at least 80%, at least 85%, at least 90%, at least 95% or higher sequence identity to SEQ ID NO: 6. In certain embodiments, the heavy chain variable region comprises the amino acid sequence having about 80%, about 85%, about 86%, about 87%, about 88%, about 89%, about 90%, about 91%, about 92%, about 93%, about 94%, about 95%, about 96%, about 97%, about 98%, or about 99% sequence identity to SEQ ID NO: 6.

In certain embodiments, the heavy chain variable region comprises the amino acid sequence shown in SEQ ID NO: 15 (humanized heavy chain variable region version 1). In certain embodiments, the heavy chain variable region comprises the amino acid sequence shown in SEQ ID NO: 16 (humanized heavy chain variable region version 2).

In certain embodiments, the light chain variable region comprises the amino acid sequence shown in SEQ ID NO: 17 (humanized light chain variable region version 1). In certain embodiments, the light chain variable region comprises the amino acid sequence shown in SEQ ID NO: 18 (humanized light chain variable region version 2). In certain embodiments, the light chain variable region comprises the amino acid sequence shown in SEQ ID NO: 19 (humanized light chain variable region version 3).

In certain embodiments, the heavy chain variable region comprises the amino acid sequence shown in SEQ ID NO: 15, and the light chain variable region comprises the amino acid sequence shown in SEQ ID NO: 17. In certain embodiments, the heavy chain variable region comprises the amino acid sequence shown in SEQ ID NO: 16, and the light chain variable region comprises the amino acid sequence shown in SEQ ID NO: 18. In certain embodiments, the heavy chain variable region comprises the amino acid sequence shown in SEQ ID NO: 16, and the light chain variable region comprises the amino acid sequence shown in SEQ ID NO: 19.

In certain embodiments, the heavy chain of the monoclonal antibody further comprises the constant region of human IgG4 or variant thereof, for example, the variant of the constant region of human IgG4 comprises the amino acid sequence shown in SEQ ID NO: 20.

In certain embodiments, the heavy chain of the monoclonal antibody comprises the amino acid sequence shown in SEQ ID NO: 21 or SEQ ID NO: 22.

In certain embodiments, the light chain of the monoclonal antibody further comprises the constant region of human Ig κ or variant thereof, for example, the constant region of human Ig κ comprises the amino acid sequence shown in SEQ ID NO: 23.

In certain embodiments, the light chain of the monoclonal antibody comprises the amino acid sequences shown in SEQ ID NO: 24, SEQ ID NO: 25 or SEQ ID NO: 26.

In certain embodiments, the monoclonal antibody comprises a heavy chain comprising the amino acid sequence shown in SEQ ID NO: 21 and a light chain comprising the amino acid sequence shown in SEQ ID NO: 24. In certain embodiments, the monoclonal antibody comprises a heavy chain comprising the amino acid sequence shown in SEQ ID NO: 22 and a light chain comprising the amino acid sequence shown in SEQ ID NO: 25. In certain embodiments, the monoclonal antibody comprises a heavy chain comprising the amino acid sequence shown in SEQ ID NO: 22 and a light chain comprising the amino acid sequence shown in SEQ ID NO: 26.

In one aspect, the present invention provides an isolated monoclonal antibody or antigen-binding fragment thereof against TFPI, which competes with the antibody comprising the light chain variable region of SEQ ID NO: 11 and the heavy chain variable region of SEQ ID NO: 6 for binding to TFPI.

In one aspect, the present invention provides an isolated monoclonal antibody or antigen-binding fragment thereof against TFPI, which competes with the antibody comprising the light chain variable region of SEQ ID NO: 11 and the heavy chain variable region of SEQ ID NO: 6 for binding to the same epitope on TFPI.

In certain embodiments, the monoclonal antibody or antigen-binding fragment thereof of the present invention specifically binds to TFPI. In certain embodiments, the monoclonal antibody or antigen-binding fragment thereof of the present invention can inhibit the interaction between FXa and TFPI.

III. Nucleic Acids, Vectors, and Methods for Producing the Antibodies

In another aspect, the present invention provides an isolated nucleic acid molecule encoding the antibody or antigen-binding fragment thereof of the present invention described above. For instance, the nucleic acid molecule may encode the light chain and/or heavy chain of the antibody or antigen-binding fragment thereof of the present invention described above.

In certain embodiments, the nucleotide sequence of the nucleic acid molecule is codon optimized for host cells used for expression.

In certain embodiments, the nucleic acid molecules comprise the nucleotide sequences shown in SEQ ID NO: 5 and/or 10.

In certain embodiments, the nucleic acid molecules of the invention are operably linked to regulatory sequences for their expression.

The present invention also provides an expression vector, which comprises the nucleic acid molecules of the invention described above.

The present invention also provides a host cell, which is transformed by the nucleic acid molecules or expression vectors of the invention described above.

In another aspect, the present invention provides a method for producing the antibodies or antigen-binding fragments thereof of the present invention, the method comprising:

(i) culturing the host cell of the present invention under conditions suitable for expression of the nucleic acid molecule or expression vector, and (ii) isolating and purifying the antibody or antigen-binding fragment thereof expressed by the host cell.

The present invention also involves the isolated antibody or antigen-binding fragment thereof obtained by the method of the present invention, which can specifically bind to TFPI and/or inhibit the interaction between FXA and TFPI.

IV Medical Uses

The monoclonal antibodies or antigen-binding fragments thereof of the present invention can be used for treating coagulation-related diseases, such as hereditary or acquired coagulation factor deficiency. For example, the monoclonal antibody or antigen-binding fragment thereof of the present invention can be used to inhibit the interaction between TFPI and FXa, or to prevent TFPI-dependent inhibition of TF/FVIIa activity. In addition, the monoclonal antibody or antigen-binding fragment of the present invention can also be used to restore FXa generation driven by TF/FVIIa, thus avoiding lack of FVIII or FIX-dependent FXa amplification.

The monoclonal antibodies or antigen-binding fragments thereof of the present invention can be used for treating coagulation-related diseases, such as thrombocytopenia, platelet disorders and bleeding disorders (for example, hemophilia, such as hemophilia A, hemophilia B and hemophilia C).

Therefore, the present invention provides a method for treating a coagulation-related disease, such as thrombocytopenia, platelet disorders and bleeding disorders (such as hemophilia such as hemophilia A, hemophilia B, and hemophilia C), which comprises administering a therapeutically effective amount of the monoclonal antibody or antigen-binding fragment thereof of the present invention to a patient in need.

The monoclonal antibody or antigen-binding fragment thereof of the present invention can also be used for treating uncontrolled bleeding in indications such as trauma and hemorrhagic stroke.

Therefore, the present invention still provides a method for shortening bleeding time, comprising administering a therapeutically effective amount of the monoclonal antibody or antigen-binding fragment thereof of the present invention to a patient in need.

The monoclonal antibodies or antigen-binding fragments thereof of that present invention can be used as monotherapy or in combination with other therapies for treating coagulation-related diseases. For example, the monoclonal antibody or antigen-binding fragment thereof of the present invention can be co-administered with coagulation factors, such as factor VII, factor VIII, or factor IX, to treat hemophilia.

Therefore, the present invention provides a method for treating a coagulation-related disease such as hereditary or acquired blood coagulation factor deficiency, which comprises administering the monoclonal antibody or antigen-binding fragment thereof of the present invention, together with blood coagulation factor(s). In certain embodiments, the coagulation factor is factor VII, factor VIII or factor IX. In certain embodiments, the hereditary or acquired coagulation factor deficiency is hemophilia, for example.

The present invention also provides a pharmaceutical composition comprising a therapeutically effective amount of the monoclonal antibodies or antigen-binding fragments thereof of the present invention, and a pharmaceutically acceptable carrier.

As used herein, a "pharmaceutically acceptable carrier" is a substance that can be added to active pharmaceutical ingredients to assist in formulating or stabilizing the preparation without causing significant adverse toxicological effects to patients, including but not limited to disintegrants, adhesives, fillers, buffers, isotonic agents, stabilizers, antioxidants, surfactants, or lubricants.

In certain embodiments, the pharmaceutical composition also includes a coagulation factor, such as factor VII, factor VIII, or factor IX.

The monoclonal antibody or antigen-binding fragment thereof of the present invention or the pharmaceutical composition of the present invention can be administered to a patient in need by injection or continuous infusion. For example, the amount of the antigen-binding fragment of the monoclonal antibody of the present invention administered by injection may be 0.0025 to 100 mg/kg, 0.025 to 0.25 mg/kg, 0.010 to 0.10 mg/kg, or 0.10 to 0.50 mg/kg body weight. For continuous infusion, the antigen-binding fragment of the monoclonal antibody of the present invention may be administered at 0.001-100 mg/kg body weight/min, 0.0125-1.25 mg/kg body weight/min, 0.010-0.75 mg/kg body weight/min, 0.010-1.0 mg/kg body weight/min or 0.10-0.50 mg/kg body weight/min for 1-24 h, 1-12 h, 2-12 h, 6-12 h, 2-8 h, or 1-2 h. For the full-length monoclonal antibody of the present invention, the administration dose may be about 1-10 mg/kg, 2-8 mg/kg, or 5-6 mg/kg body weight. Such full-length antibody is usually administered by infusion for 30 min to 3 h. The administration frequency will depend on the severity of the condition. The administration frequency may range from three times a week to once every two weeks or every three weeks.

In addition, the monoclonal antibody or antigen-binding fragment thereof of the present invention or the pharmaceutical composition of the present invention can be administered to a patient by subcutaneous injection. For instance, the monoclonal antibody or antigen-binding fragment thereof of the present invention or the pharmaceutical composition of the present invention can be administered to a patient by subcutaneous injection at a dose of 10-100 mg every week, every two weeks, or every month.

EXAMPLES

The following examples are used to further illustrate the present invention, but the scope of the present invention is not limited to these examples.

Example 1: Production of Anti-TFPI Monoclonal Antibodies 1.1 Immunization and Fusion Mice were immunized with the segmented TFPI containing only the first two Kunitz domains (SEQ ID NO: 27), and multiple mouse spleen cells with strong antibody-specific response to hTFPI antigen (SEQ ID NO: 28) were harvested for cell integration to produce hybridoma cells.

1.2 Preliminary Screening of Positive Hybridoma Cells by ELISA Binding Assays hTFPI of the same concentration was added to the ELISA plate coated by the supernatant of TFPI hybridoma cells for complete incubation, so that anti-TFPI antibodies in the supernatant of cells completely binded to hTFPI, then Anti-6×His tag antibodies labeled with peroxidase were added, followed by TMB substrate after complete incubation, peroxides were hydrolyzed by peroxidase to generate oxygen free radicals, which oxidized TMB to produce blue products, which then turned to yellow after the reaction was stopped with sulfuric acid, and the OD value was read at 450 nm. The affinity of anti-TFPI antibodies was evaluated by the OD value, the higher the OD value, the stronger the affinity. Finally, 35 cells with strong affinity to hTFPI were selected, and the specific results were shown in Table 1.

TABLE 1

| Results of binding assays of the supernatant of 35 hybridoma cells | | | | | | | |
|---|---|---|---|---|---|---|---|
| Cell strain | OD value | Cell strain | OD value | Cell strain | OD value | Cell strain | OD value |
| 1B6 | 1.908 | 8F2 | 0.854 | 6D3 | 1.954 | 10D3 | 1.057 |
| 2A1 | 1.854 | 9C6 | 1.715 | 6F5 | 1.856 | 9F11 | 0.964 |
| 2G1 | 1.933 | 9C10 | 1.473 | 6H11 | 0.854 | 6E4 | 0.344 |
| 2B2 | 1.13 | 10H7 | 1.01 | 7D1 | 1.767 | 9D6 | 0.271 |
| 2H2 | 1.223 | 6E7 | 1.679 | 7H2 | 1.641 | 9C4 | 1.622 |
| 2F6 | 1.728 | 4F10 | 1.752 | 7G6 | 1.994 | 8A9 | 1.559 |
| 2G7 | 1.493 | 3A7 | 1.796 | 7H7 | 1.763 | 5B1 | 0.034 |
| 2F9 | 1.861 | 1D6 | 1.831 | 7D9 | 1.627 | 5G1 | 0.088 |
| 4B5 | 1.886 | 10F10 | 1.756 | 8H1 | 1.768 | | |

1.3 Preliminary Screening of Positive Hybridoma Cells by Competitive ELISA Assay Coat with 2μg/mL FXA Protease (Neb, batch No. 0941404), after blocking with BSA, the same diluted supernatant of TFPI hybridoma cells and 50 ng/mL hTFPD (batch No. TE20140825, self-made) were added for complete incubation, followed by 1:1500 diluted mouse THETM His Tag Antibody [HRP] mAb (GenScript, batch No. 14C000744), after development by TMB, 1 M H2SO4 stop solution was added to stop developing and the value was read on the microplate reader. Using 650 nm as the reference wavelength, the OD values were read at 450 nm and 650 nm. The inhibition of the anti-TFPI antibody on the FXa-hTFPI binding was analyzed based on the detection data, and cell clones with superior inhibition were screened. The lower the OD value, the better the inhibition of the anti-TFPI antibody.

Table 2 showed the results of competitive assays on the supernatant of 35 hybridoma cells, among which 7G6 manifested superior inhibition.

TABLE 2

| Results of competitive assays on the supernatant of 35 hybridoma cells | | | | | | | | |
|---|---|---|---|---|---|---|---|---|
| Sample | Dilution ratio | OD | Sample | Dilution ratio | OD | Sample | Dilution ratio | OD |
| 10D3 | 10 | 1.399 | 6E4 | 10 | 1.271 | 3A7 | 10 | 1.373 |
| 10F10 | 10 | 1.405 | 6E7 | 10 | 1.234 | 4B5 | 10 | 1.36 |
| 10H7 | 10 | 1.427 | 6F5 | 10 | 1.15 | 4F10 | 10 | 1.408 |
| 1B6 | 10 | 1.193 | 6H11 | 10 | 1.305 | 5B1 | 10 | 1.191 |
| 1D6 | 10 | 1.197 | 7D1 | 10 | 1.259 | 5G1 | 10 | 1.303 |
| 2A1 | 10 | 1.094 | 7D9 | 10 | 1.253 | 6D3 | 10 | 1.157 |
| 2B2 | 10 | 1.31 | 7G6 | 10 | 0.23 | 9C10 | 10 | 1.228 |
| 2F6 | 10 | 1.237 | 7H2 | 10 | 1.386 | 9C4 | 10 | 1.296 |
| 2F9 | 10 | 1.173 | 7H7 | 10 | 1.398 | 9C6 | 10 | 1.153 |
| 2G1 | 10 | 1.258 | 8A9 | 10 | 1.31 | 9D6 | 10 | 1.365 |
| 2G7 | 10 | 1.358 | 8F2 | 10 | 1.315 | 9F11 | 10 | 1.351 |
| 2H2 | 10 | 1.319 | 8H1 | 10 | 1.114 | | | |

1.4 Determination of Subclones of Hybridoma Cells by ELISA Binding Assays

TFPI-7G6 cell strain was subcloned, and the results of ELISA binding assays showed that 31 subcloned cells manifested stronger response to hTFPI, and the assay method was the same as 1.1.

TABLE 3

| Results of binding assays on 35 TFPI-7G6 hybridoma cells | | | | | |
|---|---|---|---|---|---|
| Cell strain | OD | Cell strain | OD | Cell strain | OD |
| TFPI-7G6-1F2 | 1.362 | TFPI-7G6-1A8 | 1.27 | TFPI-7G6-2C9 | 1.293 |
| TFPI-7G6-1H3 | 1.16 | TFPI-7G6-1G8 | 1.277 | TFPI-7G6-3G1 | 1.3 |
| TFPI-7G6-1E9 | 1.335 | TFPI-7G6-1D11 | 1.244 | TFPI-7G6-3B5 | 1.292 |
| TFPI-7G6-2E3 | 1.343 | TFPI-7G6-1C12 | 1.244 | TFPI-7G6-3B6 | 1.305 |
| TFPI-7G6-2C6 | 1.367 | TFPI-7G6-4A10 | 1.243 | TFPI-7G6-3E7 | 1.422 |
| TFPI-7G6-2C12 | 1.37 | TFPI-7G6-4F9 | 1.261 | TFPI-7G6-5F9 | 1.234 |
| TFPI-7G6-2H8 | 1.493 | TFPI-7G6-4B9 | 1.251 | TFPI-7G6-5H5 | 1.227 |
| TFPI-7G6-1E7 | 1.369 | TFPI-7G6-5F11 | 1.351 | TFPI-7G6-3H11 | 1.148 |
| TFPI-7G6-2H2 | 1.301 | TFPI-7G6-5B10 | 1.053 | TFPI-7G6-4G3 | 1.197 |
| TFPI-7G6-2B8 | 1.308 | TFPI-7G6-5A10 | 1.254 | TFPI-7G6-3A6 | 1.269 |
| TFPI-7G6-2G8 | 1.268 | | | | |

Afterwards, the supernatant of 31 7G6 subcloned cells was performed with the inhibition experiment at different dilution ratios, and the experimental method was the same as 1.2.

TABLE 4

| Results of binding assays on 31 TFPI-7G6 hybridoma cells | | | | | |
|---|---|---|---|---|---|
| Sample | 100× dilution Inhibition % | 10× dilution Inhibition % | Sample | 100× dilution Inhibition % | 10× dilution Inhibition % |
| TFPI-7G6-2E3 | 65.67 | 94.99 | TFPI-7G6-2C9 | 53.17 | 94.87 |
| TFPI-7G6-3B5 | 64.09 | 95.89 | TFPI-7G6-1E9 | 51.79 | 94.87 |
| TFPI-7G6-2G8 | 62.7 | 95.89 | TFPI-7G6-1G8 | 50 | 95.12 |
| TFPI-7G6-5A10 | 62.1 | 95.89 | TFPI-7G6-4B9 | 46.63 | 94.22 |
| TFPI-7G6-2H2 | 61.71 | 95.89 | TFPI-7G6-2C12 | 33.73 | 94.35 |
| TFPI-7G6-3B6 | 61.11 | 95.89 | TFPI-7G6-3G1 | 32.14 | 94.87 |
| TFPI-7G6-5F9 | 60.91 | 95.89 | TFPI-7G6-1E7 | 14.29 | 92.43 |
| TFPI-7G6-4A10 | 60.52 | 95.76 | TFPI-7G6-3A6 | 13.89 | 93.45 |
| TFPI-7G6-1A8 | 59.72 | 94.99 | TFPI-7G6-5H5 | 10.91 | 91.91 |
| TFPI-7G6-1F2 | 59.13 | 95.12 | TFPI-7G6-2B8 | 9.52 | 92.43 |
| TFPI-7G6-2C6 | 59.13 | 95.38 | TFPI-7G6-3H11 | 3.37 | 56.48 |
| TFPI-7G6-1C12 | 57.94 | 95.25 | TFPI-7G6-4G3 | 1.79 | 71.12 |

TABLE 4-continued

| Results of binding assays on 31 TFPI-7G6 hybridoma cells | | | | | |
|---|---|---|---|---|---|
| Sample | 100× dilution Inhibition % | 10× dilution Inhibition % | Sample | 100× dilution Inhibition % | 10× dilution Inhibition % |
| TFPI-7G6-3E7 | 56.15 | 95.89 | TFPI-7G6-2H8 | −2.98 | 14.63 |
| TFPI-7G6-5F11 | 54.96 | 95.12 | TFPI-7G6-5B10 | −4.76 | 11.55 |
| TFPI-7G6-4F9 | 54.17 | 94.22 | TFPI-7G6-1H3 | −11.9 | 0.64 |
| TFPI-7G6-1D11 | 53.37 | 95.51 | | | |

Considering the inhibition effect and cell status, 7G6-2G8, 7G6-5A10, 7G6-1C12 and 7G6-5F11 were selected as the final cell strains.

Example 2: Cloning and Sequencing of Murine TFPI-7G6 Antibodies

The murine heavy chain and light chain sequences of the anti-TFPI antibody were cloned from four hybridoma cells: 7G6-2G8, 7G6-5A10, 7G6-1C12, and 7G6-5F11. Total DNA was extracted from four hybridoma cells by RANiso Plus kit (Takara), respectively, and used as the template of cDNA. 1st strand cDNA was synthesized from the total RNA using PrimeScript RTase (Takara). HC and LC variable region fragments were amplified by PCR, with A added at the terminus.

```
Amplification of LC variable region primer pair:
KF-1-EcoRV:
                                    (SEQ ID NO: 1)
GGTGATATCKTGMTSACCCAAWCTCCA KR-BamHI:
                                    (SEQ ID NO: 2)
GGGAAGATGGATCCAGTTGGTGCAGCATCAGC Amplification of HC variable region primer pair:
GF-2-PstI:
                                    (SEQ ID NO: 3)
AGGTSMAACTGCAGSAGTCWGG GR-HindIII:
                                    (SEQ ID NO: 4)
CCAGGGGCCAGTGGATAGACAAGCTTGGGTGTCGTTTT
```

PCR products were separated by gel electrophoresis, and the target gene fragments of the heavy chain and light chain variable region were recovered by AxyPrep DNA Gel Extraction Kit (AXYGEN), then linked to T-vectors and transformed into the chemically competent Mach1-T1. Colony PCR was performed on selected colonies using M13F/M13R. The positive clones were sequenced with the primer M13F(-47), and a heavy chain variable region sequence and light chain variable region sequence were determined with the specific sequence information as follows:

```
>VH nucleotide sequence
                                    (SEQ ID NO: 5)
CAGGTTCAGCTGCAGCAGTCTGGAGCTGAACTGGCGAGGCCTGGGGCT

TCAGTGAAGCTGTCCTGCAAGGCTTCTGGCTACAGCTTCACAAGTTATG

GTATAAGTTGGGTGAAGCAGAGAACTGGACAGGGCCTTGAGTGGATCGG

AGAGATTTATCCTAGAAGTACTAATACTTACTACAATGAGAAGTTCATG

GGCAAGGCCACACTGACTGCAGACAAATCCTCCAGCACAGCGTTCATGG

AGCTCCGCAGCCTGACATCTGAGGACTCTGCGGTCTATTTCTGTGCAAG

AGAATCCTTCTATGGTGACTATGGGGCTATGGACTTCTGGGGTCAGGGA

GCCTCAGTCACCGTCTCCTCA

>VH amino acid sequence
                                    (SEQ ID NO: 6)
QVQLQQSGAELARPGASVKLSCKASGYSFTSYGISWVKQRTGQGLEWIG

EIYPRSTNTYYNEKFMGKATLTADKSSSTAFMELRSLTSEDSAVYFCAR

ESFYGDYGAMDFWGQGASVTVSS

>VH CDR1
                                    (SEQ ID NO: 7)
SYGIS

>VH CDR2
                                    (SEQ ID NO: 8)
EIYPRSTNTYYNEKFMG

>VH CDR3
                                    (SEQ ID NO: 9)
ESFYGDYGAMDF

>VL nucleotide sequence
                                    (SEQ ID NO: 10)
GATATCGTGCTGACCCAATCTCCACTCACTTTGTCGGTTACCATTGGAC

AACCAGCCTCCATCTTTTGCAAGTCAAGTCAGAGCCTCTTAGAAAGTGA

TGGAAAGACATATTTGAATTGGTTGTTGCAGAGGCCAGGCCAGTCTCCA

AAGCGCCTTATCTATCTGGTGTCTAAACTGGACTCTGGAGTCCCTGACA

GGTTCACTGGCAGTGGATCAGGGACAGATTTCACACTGAAGATCAGCAG

AGTGGAGGCTGAGGATTTGGGAGTTTATTATTGCTGCCAAGGTACACAT

TTTCCTCGGACGTTCGGTGGAGGCACCAAGCTGGAAATCAAACGG

>VL amino acid sequence
                                    (SEQ ID NO: 11)
DIVLTQSPLTLSVTIGQPASIFCKSSQSLLESDGKTYLNWLLQRPGQSP

KRLIYLVSKLDSGVPDRFTGSGSGTDFTLKISRVEAEDLGVYYCCQGTH

FPRTFGGGTKLEIKR

>VL CDR1
                                    (SEQ ID NO: 12)
KSSQSLLESDGKTYLN
```

18
-continued

```
>VL CDR2
                                    (SEQ ID NO: 13)
LVSKLDS

>VL CDR3
                                    (SEQ ID NO: 14)
QGTHFPRT
```

Example 3 Design and Construction of Humanized TFPI-7G6 Antibodies 3.1 Humanization of TFPI-7G6 antibodies The humanization method was achieved by humanization of amino acids on the protein surface (resurfacing) and CDR grafting to a universal framework for VH and VL humanization.

The humanization steps were as follows: subjecting the VH and VL of antibody strain 7G6 to homologous modeling by the software Modeller 9, respectively. Make a reference to PDB serial numbers of VL homologous sequences: 1nldL, VLK2; PDB serial numbers of VH homologous sequences: 1xgyI and VH1B. Afterwards, according to KABAT numbering, the CDR region was grafted to the framework of the humanized homologous sequence. Meanwhile, the relative solvent accessibility of amino acids was calculated based on the three-dimensional structure of protein. Amino acids that are not exposed to the solvent can be appropriately replaced by amino acids in the same position of the original antibody sequence.

TFPI-7G6 was humanized, and two different humanized sequences for the heavy chain were obtained: h7G6VH-v1 (Seq ID No: 15) and hu7G6VH-v2 (Seq ID No: 16), and three different humanized sequences for the light chain were obtained: h7G6VL-v1 (SEQ ID NO: 17), h7G6VL-v2 (SEQ ID NO: 18), and 7G6VL-v3 (SEQ ID NO: 19). FIG. 1 listed the alignment results between these humanized variants and murine antibodies.

3.2 Preparation of Expression Vectors of Humanized h7G6

According to the humanized design of the antibodies mentioned above, the DNA sequences of humanized h7G6-2-VH1, h7G6-2-VH2, h7G6-2-VL1, h7G6-2-VL2 and h7G6-2-VL3 were synthesized (GENEWIZ). The construct contained each of LC and HC signal peptides and Kozak sequence (5'-GCCACC-3') immediately upstream of the start codon.

Based on the amino acid sequence (P01861) of the constant region of human IgG4 in the protein database uniprot, in order to eliminate the formation of monomer antibody fragment (that is, a "half antibody" composed of one LC and one HC), the amino acid sequence (SEQ ID NO: 20) of human IgG4-Fc region was obtained by replacing Ser with Pro at position 108. The nucleic acid fragment encoding human IgG4-Fc was obtained through codon optimization and gene synthesis, then subjected to digestion and ligation to give the coded amino acid fragment of the heavy chain variable region of h7G6 antibody obtained in the above example, which was then cloned into the conventional mammalian expression vector to obtain heavy chain 1 (SEQ ID NO: 21) and heavy chain 2 (SEQ ID NO: 22) of h7G6 antibody. The sequence of the final construct was verified by DNA sequencing.

According to the amino acid sequence of the constant region of human Ig (P01834) in the protein database uniprot, the amino acid sequence of the constant region of human Ig κ (SEQ ID NO: 23) was obtained. The nucleic acid fragment encoding the constant region of human Ig κ was obtained through codon optimization and gene synthesis, then subjected to digestion and ligation to give the coded amino acid fragment of the light chain variable region of h7G6 antibody obtained in the above example, which was then cloned into the conventional mammalian expression vector to obtain light chain 1 (SEQ ID NO: 24) and light chain 2 (SEQ ID NO: 25), and light chain 3 (SEQ ID NO: 26) of h7G6 antibody. The sequence of the final construct was verified by DNA sequencing.

3.3 Selection of Plasmid Combinations for Protein Expression

A mixture of 0.2 ug HC vector DNA +0.3 ug LC vector DNA was used per mL of cell culture. The combination of antibody heavy chain 1 and antibody light chain 1 was Hu7G61, the combination of antibody heavy chain 2 and antibody light chain 2 was Hu7G62-v1, and the combination of antibody heavy chain 2 and antibody light chain 3 was Hu7G62-v2. HEK293 cells were transfected with mixed DNA for antibody expression. Meanwhile, comparison with the original mouse antibody was performed. The expression levels and purity of the three humanized sequences and the original murine sequence were shown in the following table:

TABLE 5

| Antibody | Expression level | Purity by SEC |
|---|---|---|
| 7G6 | 15 mg/L | 91.3% |
| Hu7G61 | 7 mg/L | 90% |
| Hu7G62-v1 | 30 mg/L | 99.2% |
| Hu7G62-v2 | 140 mg/L | 98.7% |

The results showed that all the three humanized antibodies were capable of being expressed with purity >90%. Among these, the expression level and purity of the last two humanized sequences were obviously superior to that of the maternal murine antibody. And the last humanized antibody Hu7G62-v2 manifested the highest expression level.

3.4 Preparation of h7G6 Antibody Protein

HEK293 cells were transfected with a plasmid mixture of antibody heavy chain 2 and antibody light chain 3 for antibody expression. The recombinant expression plasmid was diluted with Freestyle293 medium and added with PEI (Polyethylenimine) solution needed for transformation, and each group of plasmid/PEI mixture was added into HEK293 cell suspension and cultured at 37° C., 10% $CO_2$, 90 rpm; meanwhile, 50 µg/L IGF-1 was added. Four hours later, EX293 medium, 2 mM glutamine and 50 µg/L IGF-1 were added for culture at 135 rpm. 24 hours later, 3.8 mM VPA was added. After culture for 5-6 days, the supernatant of transient expression culture was collected, and the target hu7G6 protein was obtained by purification using Protein A affinity chromatography.

Example 4: Verifying Functions of hu7G6 Antibody Proteins

FIG. 4.1 Affinity of humanized h7G6 antibodies for hTFPI.

1) ELISA Method hTFPI161 protein was coated on the plate at 0.5 µg/well overnight at 4° C. After washing, the gradient dilution series of h7G6 antibody protein obtained in the above example was added, and incubated at 25° C±2° C. for 2 h. After washing, 1:2000 diluted Mouse Anti-Human IgG4 pFc' antibody [HP 6023] (HRP) was added at 100 µL/well, and incubated at 25° C.±2° C. for 2 h. After washing, the development solution was added, and the absorbance was read at the wavelength of 450/650 nm. The software SotfMax Pro v5.4 was applied for data processing and mapping analysis, using four-parameter fitting, the binding curve of h7G6 antibody to hTFPI161 and EC50 value were obtained, which reflects the affinity of the antibody for hTFPI161.

The results were shown in the following table and FIG. 2, in which the ordinate was OD450 and the abscissa is the concentration of h7G6 antibody protein (ng/mL); and Hu7G62-v2 antibody protein showed superior affinity for hTFPI161.

TABLE 6

| Conc (ng/mL) | hu7G6-2v2-G4ws |
|---|---|
| 10000 | 2.785 |
| 3333.333 | 2.775 |
| 1111.111 | 2.824 |
| 370.37 | 2.816 |
| 123.457 | 2.189 |
| 41.152 | 1.399 |
| 13.717 | 0.677 |
| 4.572 | 0.279 |
| 1.524 | 0.106 |
| 0.508 | 0.048 |
| 0.169 | 0.027 |
| $EC_{50}$ (ng/mL) | 41.9 |

2) Detection by Bio-layer Interferometry

In this experiment, the affinity of h7G6 for human TFPI was detected based on Bio-Layer Interferometry (BLI) technology. K2 instrument of Fortibio was used. Firstly, KN057 was diluted to 10 m/mL and immobilized on Protein A biosensor (model 18-5010), then hTFPI161-Chis was diluted to 30 nM, 15 nM, 7.5 nM, 3.75 nM and 1.875 nm to combine with h7G6, respectively, and the binding signals with different intensities could be detected. The results were fitted using 1:1 model to calculate the equilibrium constant (KD) of the sample. The analysis results were as follows: the KD values of three batches of h7G6 stock solution (180727DS, 180808DS, 180820DS) for human TFPI were 1.32 E-09 M, 1.32 E-09 M and 1.47 E-09 M, respectively, the average KD is (1.37±0.09) E-09 M, and RSD% was 6.32%.

4.2 Inhibition of the Interaction between FXa and TFPI by the Humanized hu7G6 Antibodies FXa Protease was coated on the plate at 0.2 µg/well overnight at 4° C., after blocking with BSA, the gradient dilution series of hu7G6 antibody protein obtained from the above example was added at 100 uL/well (50 ng/mL hTFPI161 was contained in the dilution), and the reaction was carried out at room temperature for 1 hour. After washing, 1:1500 diluted Mouse THETM His Tag Antibody [HRP] mAb was added, and the reaction was carried out at room temperature for 1 hour. After washing, the development solution was added, and the absorbance was read at the wavelength of 450/650 nm.

Figure 3:
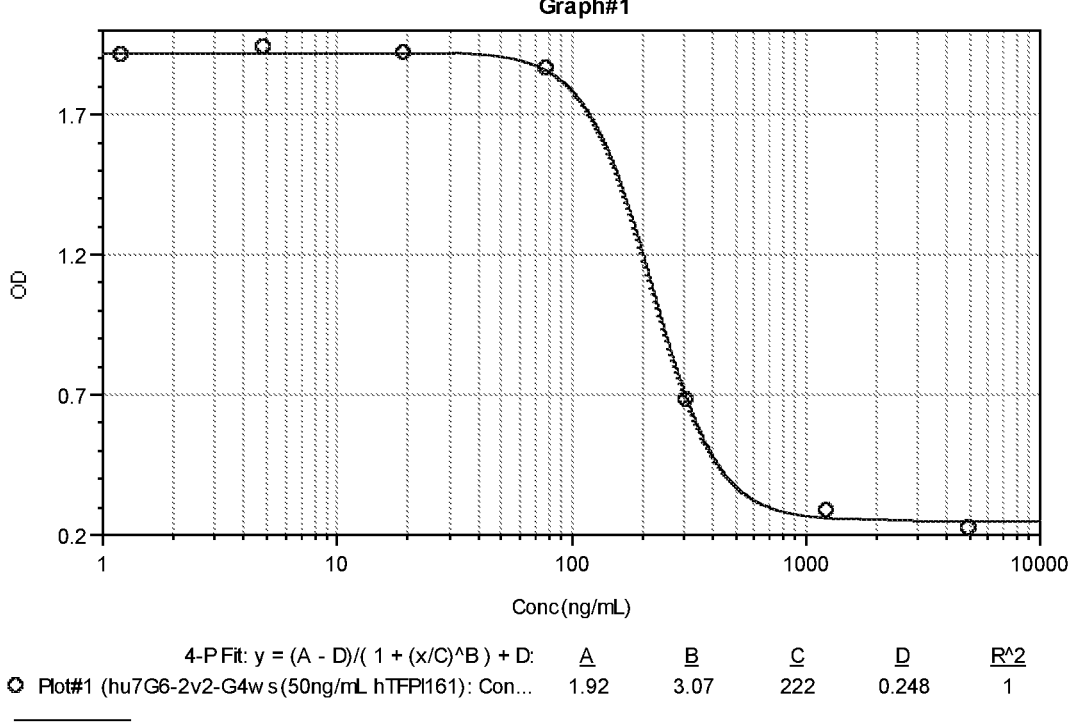
FIG. 3 shows the inhibition of the FXa-TFPI interaction by the humanized h7G6 antibody.

The software SotfMax Pro v5.4 was applied for data processing and mapping analysis, using four-parameter fitting, the inhibition curve of h7G6 antibody for FXa-TFPI and EC50 value were obtained. The results were shown in FIG. 3, in which the ordinate was OD450 and the abscissa is the concentration of h7G6 antibody protein (ng/mL); and Hu7G62-v2 antibody protein was effective in inhibiting the interaction between FXA and TFPI.

TABLE 7

Inhibition of h7G6 antibody for the
interaction between FXa and TFPI

| Conc (ng/mL) | hu7G6-2v2 (50 ng/mL hTFPI161) |
|---|---|
| 5000 | 0.220 |
| 1250 | 0.285 |
| 312.5 | 0.679 |
| 78.125 | 1.859 |
| 19.531 | 1.917 |
| 4.883 | 1.934 |
| 1.221 | 1.908 |
| $IC_{50}$ (ng/mL) | 222 |

Example 5: In Vivo Studies

28 New Zealand rabbits were randomly divided into 4 groups based on body weight: 1—normal control group (n=4); 2—model control group (n=8); 3—positive control group (n=8), and 4—test group (n=8), half male and half female. After anesthesia, except animals from the normal control group, all the other animals were injected via the marginal ear vein with 600 µg/kg BO2C11 antibody (human coagulation factor VIII-neutralizing antibody, the sequence thereof was retrieved from the following literature: Structure of a factor VIII C2 domain—immunoglobulin G4k Fab complex: identification of an inhibitory antibody epitope on the surface of factor VIII) to establish a New Zealand rabbit model of hemophilia A. 10 min after modeling, 2 mg/kg of the test sample (h7G6 antibody protein) or the control sample (TFPI2021, a control antibody from Novartis) was injected intravenously via the marginal ear vein, and PBS of a corresponding volume were administrated to the normal control group and model control group. 25 min after administration, the left forelimb of the animal was preheated in a solution containing 45 mL normal saline at 37° C., 10 min later, the top of the third toenail of the left forelimb of the animal was cut off with a surgical scissor, while bleeding, the stopwatch was started to measure the bleeding time, and stopped until the time when no bloodshot oozed from the wound was observed, which was considered the end point of this coagulation observation, the bleeding time was recorded.

The results of Table 8 showed that the bleeding time was significantly increased from normal 6.3±2.3 min (control group) to 28.1±14.4 min (model group); both the test sample and the positive control sample were capable of reducing the bleeding time of New Zealand rabbits with hemophilia A after administration, and manifesting similar functions, which indicated that Hu7G62-v2 antibody was effective in the treatment of rabbits with hemophilia A.

TABLE 8

Bleeding time of each group of animals

| Group | bleeding time (min) |
|---|---|
| normal control group | 6.3 ± 2.3 |
| model control group | 28.1 ± 14.4 |
| positive control group | 11.3 ± 6.6 |
| test group | 14.8 ± 7.0 |

Example 6: Estimation of Dose-effect Relationship

After anesthesia, New Zealand rabbits were injected intravenously with 1 mg/kg anti-FVIII antibody (BO2C11) via the marginal ear vein to establish a New Zealand rabbit model with induced hemophilia A. 10 min after modeling, different concentrations (2/20 mg/kg) of Hu7G62-v2 antibodies were injected intravenously via the marginal ear vein. 35 min later, the top of the third toenail of the left forelimb of the animal was cut off, the bleeding time was started while bleeding, and stopped until the time when no bloodshot oozed from the wound was observed, which was considered the end point of this coagulation observation. The observation upper limit of bleeding time of animals was 60 min, if the bleeding time exceeded 60 min, then it was recorded as 60 min. See Table 9 for specific grouping and administration information.

TABLE 9

Information of grouping and administration

| Group | | Dosage (mg/kg) | Dosing concentration (mg/mL) | Dosing volume (mL/kg) |
|---|---|---|---|---|
| 1 | Blank control group | — | — | 1.0 |
| 2 | BO2C11 | 1 | 2.5 | 0.4 |
| 3 | BO2C11+ h7G6 antibody | 1 + 2 | 2.5 + 2 | 0.4 + 1.0 |
| 4 | BO2C11+ h7G6 antibody | 1 + 20 | 2.5 + 20 | 0.4 + 1.0 |

The results were shown in Table 10: Compared with the control group, the bleeding time of rabbits injected with anti-F VIII antibody was significantly prolonged (P <0.01), increasing from the normal 6.0±1.9 min to 54.0±13.4 min. After administration of different concentrations of h7G6 antibody by single intravenous injection, the bleeding time of animals was significantly shortened (P<0.05), showing a certain degree of dose dependence. Detection of hemoglobin can be indicative of the bleeding volume of animals during the observation, and the results showed that the hemoglobin content increased significantly after modeling, but decreased after injection with h7G6 antibody, showing that h7G6 antibody enabled the reduced bleeding time as well as the less risk of bleeding.

TABLE 10

Bleeding time and hemoglobin content

| Group | Dosage/ mg/kg | Bleeding time/min | Hemoglobin (mM) |
|---|---|---|---|
| Control group | — | 6.0 ± 1.9 | 11.6 ± 9.7 |
| BO2C11 model group | 1 | 54.0 ± 13.4## | 66.2 ± 25.6 |
| BO2C11+ h7G6 antibody, low dose | 1 + 2 | 18.0 ± 3.4* | 25.8 ± 18.1 |
| BO2C11+ h7G6 antibody, high dose | 1 + 20 | 12.2 ± 4.8** | 44.8 ± 45.1 |

Compared with the control group, P < 0.01;
*Compared with the model group, P < 0.05;
**Compared with the model group, P < 0.01

Example 7: Pharmacokinetic Evaluations of Anti-TFPI Antibodies in Cynomolgus Monkeys in vivo The purpose of this experiment was to determine the drug concentration of the anti-TFPI antibody in the plasma of cynomolgus monkeys after single subcutaneous multi-dose administration and single intravenous administration, respectively, and to examine pharmacokinetic characteristics thereof in the cynomolgus monkeys in vivo. Meanwhile, the exposure differences of anti-TFPI antibodies in the cynomolgus monkeys after intravenous administration and subcutaneous administration were compared and the absolute bioavailability was calculated.

The cynomolgus monkeys are divided into four groups, each containing three females and three males. Administration was carried out according to the following dosages and ways. The number of administration was once. The plasma drug concentration was examined by blood sampling before administration and in 0.5 h, 2 h, 4 h, 8 h, 24 h, 48 h, 72 h (3 days), 96 h (4 days), 120 h (5 days), 144 h (6 days), 168 h (7 days), 216 h (9 days), 264 h (11 days) after subcutaneous injection.

TABLE 11

Experimental design of pharmacokinetic evaluations

| Group | Test sample | Dosing route | Number and sex of animals (Male/Female) | Dosing plan | Dosage (mg/kg) |
|---|---|---|---|---|---|
| 1 (low dose) | KN057 | Subcutaneous injection | 3/3 | Single | 1 |
| 2 (medium dose) | KN057 | Subcutaneous injection | 3/3 | Single | 3 |
| 3 (high dose) | KN057 | Subcutaneous injection | 3/3 | Single | 10 |
| 4 (high dose) | KN057 | Intravenous injection | 3/3 | Single | 10 |

The relevant pharmacokinetic parameters were calculated by Phoenix software (version 8.1) based on the obtained plasma drug concentration data.

The results were shown in the following table.

TABLE 12

Experimental results of pharmacokinetic evaluations

| Parameter | Unit | Group 1 1 mg/kg (Subcutaneous injection) Average (N = 3/sex) | Group 2 3 mg/kg (Subcutaneous injection) Average (N = 3/sex) | Group 3 10 mg/kg (Subcutaneous injection) Average (N = 3/sex) | Group 4 10 mg/kg (Intravenous injection) Average (N = 3/sex) |
|---|---|---|---|---|---|
| $C_{max}$ | [μg/mL] | 2.12 | 15.6 | 70.1 | 213.5 |
| $T_{max}$ | [hr] | 10.7 | 36.0 | 60.0 | N.C |
| $T_{1/2}$ | [hr] | 52.2 | 37.6 | 58.4 | 63.3/47.2 |
| $AUC_{norm}$ | [(hr · kg)/L] | 101 | 680 | 1630 | 2415 |

TABLE 12-continued

Experimental results of pharmacokinetic evaluations

| Parameter | Unit | Group 1 1 mg/kg (Subcutaneous injection) Average (N = 3/sex) | Group 2 3 mg/kg (Subcutaneous injection) Average (N = 3/sex) | Group 3 10 mg/kg (Subcutaneous injection) Average (N = 3/sex) | Group 4 10 mg/kg (Intravenous injection) Average (N = 3/sex) |
|---|---|---|---|---|---|
| CL | [mL/hr/kg] | — | — | — | 0.43 |
| Vss | [mL/kg] | — | — | — | 32.8 |
| $MRT_{INF}$ | [hr] | 42.2 | 81.3 | 164 | 151.5 |
| F | % | — | — | 67.5 | — |

The relevant parameters were explained as follows:
$T_{1/2}$ Elimination half-life
Cmax Maximum plasma drug concentration
$T_{max}$ The time to maximum plasma drug concentration
$AUC_{norm}$ The ratio of the area under the plasma concentration-time curve to dosage
CL Clearance
MRT Mean residence time
Vss Apparent volume of distribution
F% Absolute bioavailability %

By comparing the results with the pharmacokinetic data of Bayer TFPI antibody BAY1093884 in cynomolgus monkeys published by Jian-Ming Gu et al. in 2017 (Refer to Gu J, Zhao X, Schwarz T, et al. Mechanistic Modeling of the Pharmacodynamic and Pharmacokinetic Relationship of Tissue Factor Pathway Inhibitor-Neutralizing Antibody (BAY 1093884) in Cynomolgus Monkeys[J]. Aaps Journal, 2017, 19(4): 1186-1195), the half-life in vivo and mean drug retention time of the anti-TFPI antibody of the present invention injected subcutaneously at a dose of 3 mg/kg or more were significantly higher than that of BAY1093884 injected subcutaneously at 5 mg/kg (T1/2=25 hr, MRT=40 hr for BAY1093884), and the relative drug exposure thereof was also significantly higher than that of BAY1093884 (AUCnorm=517 kg hr/L). Meanwhile, when the anti-TFPI antibody of the present invention was injected intravenously at a dose of 10 mg/kg, the plasma drug clearance rate thereof was obviously lower than that of BAY1093884 injected intravenously at a dose of 5 mg/kg and 20 mg/kg (5 mg/mL dosing group: 1.2 mL/hr/kg; 20 mg/kg dosing group: 0.6 mL/hr/kg). The above results show that compared with Bayer's BAY1093884, the anti-TFPI antibody of the present invention has longer circulation time and slower clearance in vivo; the lower the dose, the better the drug exposure.

The invention claimed is:

1. An isolated monoclonal antibody or antigen-binding fragment thereof against TFPI, wherein the monoclonal antibody comprises a light chain variable region and a heavy chain variable region, wherein:

the light chain variable region comprises:

VL CDR1 comprising the amino acid sequence shown in SEQ ID NO: 12,

VL CDR2 comprising the amino acid sequence shown in SEQ ID NO: 13, and

VL CDR3 comprising the amino acid sequence shown in SEQ ID NO: 14; and the heavy chain variable region comprises:

VH CDR1 comprising the amino acid sequence shown in SEQ ID NO: 7,

VH CDR2 comprising the amino acid sequence shown in SEQ ID NO: 8, and

VH CDR3 comprising the amino acid sequence shown in SEQ ID NO: 9.

2. The isolated monoclonal antibody or antigen-binding fragment thereof according to claim 1, wherein the isolated monoclonal antibody is a humanized antibody.

3. The isolated monoclonal antibody or antigen-binding fragment thereof according to claim 1, wherein the light chain variable region comprises the amino acid sequence shown in SEQ ID NO: 11 or an amino acid sequence having at least 80%, at least 85%, at least 90%, at least 95% or higher sequence identity to SEQ ID NO: 11.

4. The isolated monoclonal antibody or antigen-binding fragment thereof according to claim 1, wherein the heavy chain variable region comprises the amino acid sequence shown in SEQ ID NO: 6 or an amino acid sequence having at least 80%, at least 85%, at least 90%, at least 95% or higher sequence identity to SEQ ID NO: 6.

5. The isolated monoclonal antibody or antigen-binding fragment thereof according to claim 2, wherein the heavy chain variable region comprises the amino acid sequence shown in SEQ ID NO: 15 or SEQ ID NO: 16.

6. The isolated monoclonal antibody or antigen-binding fragment thereof according to claim 2, wherein the light chain variable region comprises the amino acid sequence as set forth in any of SEQ ID NOs: 17-19.

7. The isolated monoclonal antibody or antigen-binding fragment thereof according to claim 2, wherein the heavy chain variable region comprises the amino acid sequence shown in SEQ ID NO: 15, and the light chain variable region comprises the amino acid sequence shown in SEQ ID NO: 17.

8. The isolated monoclonal antibody or antigen-binding fragment thereof according to claim 2, wherein the heavy chain variable region comprises the amino acid sequence shown in SEQ ID NO: 16, and the light chain variable region comprises the amino acid sequence shown in SEQ ID NO: 18.

9. The isolated monoclonal antibody or antigen-binding fragment thereof according to claim 2, wherein the heavy chain variable region comprises the amino acid sequence shown in SEQ ID NO: 16, and the light chain variable region comprises the amino acid sequence shown in SEQ ID NO: 19.

10. The isolated monoclonal antibody or antigen-binding fragment thereof according to claim 5, wherein the heavy chain of the monoclonal antibody further comprises the constant region of human IgG4 or a variant thereof, optionally wherein the variant of the constant region of human IgG4 comprises the amino acid sequence shown in SEQ ID NO: 20.

11. The isolated monoclonal antibody or antigen-binding fragment thereof according to claim 10, wherein the heavy chain comprises the amino acid sequence shown in SEQ ID NO: 21 or SEQ ID NO: 22.

12. The isolated monoclonal antibody or antigen-binding fragment thereof according to claim 6, wherein the light chain of the monoclonal antibody further comprises the constant region of human Ig κ or a variant thereof, optionally wherein the constant region of human Ig κ comprises the amino acid sequence shown in SEQ ID NO: 23.

13. The isolated monoclonal antibody or antigen-binding fragment thereof according to claim 12, wherein the light chain comprises the amino acid sequence selected from SEQ ID NO: 24, SEQ ID NO: 25, and SEQ ID NO: 26.

14. The isolated monoclonal antibody or antigen-binding fragment thereof according to claim 10, wherein the monoclonal antibody comprises a heavy chain comprising the amino acid sequence shown in SEQ ID NO: 21, and a light chain comprising the amino acid sequence shown in SEQ ID NO: 24.

15. The isolated monoclonal antibody or antigen-binding fragment thereof according to claim 10, wherein the monoclonal antibody comprises a heavy chain comprising the amino acid sequence shown in SEQ ID NO: 22, and a light chain comprising the amino acid sequence shown in SEQ ID NO: 25.

16. The isolated monoclonal antibody or antigen-binding fragment thereof according to claim 10, wherein the monoclonal antibody comprises a heavy chain comprising the amino acid sequence shown in SEQ ID NO: 22, and a light chain comprising the amino acid sequence shown in SEQ ID NO: 26.

17. A pharmaceutical composition for treating hemophilia A or hemophilia B, comprising a therapeutically effective amount of the monoclonal antibody or antigen-binding fragment thereof according to claim 1, and a pharmaceutically acceptable carrier.

18. The pharmaceutical composition according to claim 17, further comprising a coagulation factor, optionally factor VII, factor VIII, or factor IX.

19. A method for treating a coagulation-related disease in a subject in need thereof, the method comprising administering a therapeutically effective amount of the isolated monoclonal antibody or antigen-binding fragment thereof according to claim 1 to the subject to thereby treat the coagulation-related disease in the subject, wherein the coagulation-related disease is hemophilia A or hemophilia B.

\* \* \* \* \*